US011793399B2

(12) United States Patent
Talbert et al.

(10) Patent No.: US 11,793,399 B2
(45) Date of Patent: Oct. 24, 2023

(54) SUPER RESOLUTION AND COLOR MOTION ARTIFACT CORRECTION IN A PULSED HYPERSPECTRAL IMAGING SYSTEM

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International, Zug (CH)

( * ) Notice: Subject to any disclaimer, the term of this patent is extended or adjusted under 35 U.S.C. 154(b) by 740 days.

(21) Appl. No.: 16/719,157

(22) Filed: Dec. 18, 2019

(65) Prior Publication Data
US 2020/0397350 A1 Dec. 24, 2020

Related U.S. Application Data

(60) Provisional application No. 62/864,213, filed on Jun. 20, 2019.

(51) Int. Cl.
A61B 1/06 (2006.01)
A61B 5/1455 (2006.01)
(Continued)

(52) U.S. Cl.
CPC ...... A61B 1/0638 (2013.01); A61B 1/000095 (2022.02); A61B 1/043 (2013.01);
(Continued)

(58) Field of Classification Search
None
See application file for complete search history.

(56) References Cited

U.S. PATENT DOCUMENTS 3,844,047 A 10/1974 Carson
4,419,583 A 12/1983 Noeller
(Continued)

FOREIGN PATENT DOCUMENTS

CA 2592691 C * 7/2017 ........... A61B 5/0059
JP H04158205 A 6/1992
(Continued)

OTHER PUBLICATIONS

USPTO, International Search Report for PCT/US2020/36152 (Year: 2020).*

(Continued)

Primary Examiner — David N Werner
(74) Attorney, Agent, or Firm — Terrence J. Edwards; TechLaw Ventures, PLLC

(57) ABSTRACT

Super resolution and color motion artifact correction in a pulsed hyperspectral imaging system. A method includes actuating an emitter to emit a plurality of pulses of electromagnetic radiation and sensing reflected electromagnetic radiation with a pixel array of an image sensor to generate a plurality of exposure frames. The method includes detecting motion across two or more sequential exposure frames, compensating for the detected motion, and combining the two or more sequential exposure frames to generate an image frame. The method is such that at least a portion of the plurality of pulses of electromagnetic radiation emitted by the emitter comprises one or more of electromagnetic radiation having a wavelength from about 513 nm to about 545 nm, from about 565 nm to about 585 nm, or from about 900 nm to about 1000 nm.

30 Claims, 23 Drawing Sheets

(51) Int. Cl.
    *H04N 5/14*     (2006.01)
    *A61B 5/00*     (2006.01)
    *G06T 7/00*     (2017.01)
    *A61B 1/00*     (2006.01)
    *H04N 23/56*     (2023.01)
    *A61B 1/04*     (2006.01)

(52) U.S. Cl.
    CPC ............ *A61B 1/046* (2022.02); *A61B 1/0655* (2022.02); *A61B 5/0028* (2013.01); *A61B 5/1455* (2013.01); *G06T 7/0016* (2013.01); *H04N 5/145* (2013.01); *H04N 23/56* (2023.01)

(56) References Cited

U.S. PATENT DOCUMENTS

| | | |
|---|---|---|
| 4,556,057 A | 12/1985 | Hiruma et al. |
| 5,318,024 A | 6/1994 | Kittrell et al. |
| 5,363,387 A | 11/1994 | Sinofky |
| 5,515,449 A | 5/1996 | Tsuruoka et al. |
| 5,692,062 A | 11/1997 | Lareau et al. |
| 5,749,830 A | 5/1998 | Kaneko et al. |
| 5,784,162 A | 7/1998 | Cabib et al. |
| 5,903,996 A | 5/1999 | Morley |
| 6,061,591 A | 5/2000 | Freitag et al. |
| 6,110,106 A | 8/2000 | MacKinnon et al. |
| 6,236,879 B1 | 5/2001 | Konings |
| 6,345,194 B1 | 2/2002 | Nelson et al. |
| 6,448,545 B1 | 9/2002 | Chen |
| 6,537,211 B1 | 5/2003 | Wang et al. |
| 6,899,675 B2 | 5/2005 | Cline et al. |
| 6,975,898 B2 | 12/2005 | Seibel |
| 7,235,045 B2 | 6/2007 | Wang et al. |
| 7,302,174 B2 | 11/2007 | Tan et al. |
| 7,428,048 B1 | 9/2008 | Farkas et al. |
| 8,073,528 B2 | 12/2011 | Zhao et al. |
| 8,167,793 B2 | 5/2012 | Scott et al. |
| 8,471,915 B2 | 6/2013 | Robinson et al. |
| 9,509,917 B2 | 11/2016 | Blanquart et al. |
| 9,516,239 B2 | 12/2016 | Blanquart et al. |
| 9,641,815 B2 | 5/2017 | Richardson et al. |
| 11,006,093 B1 | 5/2021 | Hegyi |
| 11,276,148 B2 | 3/2022 | Talbert et al. |
| 11,280,737 B2 | 3/2022 | Talbert et al. |
| 11,288,772 B2 | 3/2022 | Talbert et al. |
| 11,360,028 B2 | 6/2022 | Talbert et al. |
| 11,398,011 B2 | 7/2022 | Talbert et al. |
| 2001/0000317 A1 | 4/2001 | Yoneya et al. |
| 2002/0016533 A1 | 2/2002 | Marchitto et al. |
| 2002/0065468 A1 | 5/2002 | Utzinger et al. |
| 2002/0123666 A1 | 9/2002 | Matsumoto |
| 2002/0138008 A1 | 9/2002 | Tsujita et al. |
| 2002/0139920 A1 | 10/2002 | Seibel et al. |
| 2002/0161282 A1 | 10/2002 | Fulghum |
| 2003/0100824 A1 | 5/2003 | Warren et al. |
| 2003/0223248 A1 | 12/2003 | Cronin et al. |
| 2004/0010192 A1 | 1/2004 | Benaron et al. |
| 2004/0116800 A1 | 6/2004 | Helfer et al. |
| 2004/0186351 A1 | 9/2004 | Imaizumi et al. |
| 2004/0234152 A1 | 11/2004 | Liege et al. |
| 2005/0020926 A1 | 1/2005 | Wiklof et al. |
| 2005/0107808 A1 | 5/2005 | Evans et al. |
| 2005/0205758 A1 | 9/2005 | Almeida |
| 2006/0069314 A1 | 3/2006 | Farr |
| 2006/0239723 A1 | 10/2006 | Okuda et al. |
| 2006/0276966 A1 | 12/2006 | Cotton et al. |
| 2007/0016077 A1 | 1/2007 | Nakaoka et al. |
| 2007/0046778 A1 | 3/2007 | Ishihara et al. |
| 2007/0057211 A1 | 3/2007 | Bahlman et al. |
| 2007/0081168 A1 | 4/2007 | Johnston |
| 2007/0086495 A1 | 4/2007 | Sprague et al. |
| 2007/0177009 A1 | 8/2007 | Bayer et al. |
| 2007/0206187 A1 | 9/2007 | Lundquist |
| 2007/0242330 A1 | 10/2007 | Rosman et al. |
| 2007/0276234 A1 | 11/2007 | Shahidi |
| 2008/0058629 A1 | 3/2008 | Seibel et al. |
| 2008/0081950 A1 | 4/2008 | Koenig et al. |
| 2008/0090220 A1 | 4/2008 | Freeman et al. |
| 2008/0177139 A1 | 7/2008 | Courtney et al. |
| 2008/0192231 A1 | 8/2008 | Jureller et al. |
| 2008/0249368 A1 | 10/2008 | Takei |
| 2008/0318307 A1 | 12/2008 | Spittle et al. |
| 2009/0067458 A1 | 3/2009 | Ji et al. |
| 2009/0289200 A1 | 11/2009 | Ishii |
| 2009/0303317 A1 | 12/2009 | Tesar |
| 2009/0306478 A1 | 12/2009 | Mizuyoshi |
| 2010/0049180 A1 | 2/2010 | Wells et al. |
| 2010/0056928 A1 | 3/2010 | Zuzak et al. |
| 2010/0128109 A1 | 5/2010 | Banks |
| 2010/0134607 A1 | 6/2010 | Ishihara |
| 2010/0157039 A1 | 6/2010 | Sugai |
| 2010/0160917 A1 | 6/2010 | Fitz et al. |
| 2010/0168585 A1 | 7/2010 | Fujii |
| 2010/0261958 A1 | 10/2010 | Webb et al. |
| 2010/0277087 A1 | 11/2010 | Ikeda |
| 2010/0297659 A1 | 11/2010 | Yoo |
| 2011/0017217 A1 | 1/2011 | Wood et al. |
| 2011/0087212 A1 | 4/2011 | Aldridge et al. |
| 2011/0196355 A1 | 8/2011 | Mitchell et al. |
| 2011/0206075 A1 | 8/2011 | Ji et al. |
| 2011/0213252 A1 | 9/2011 | Fulghum |
| 2011/0270092 A1* | 11/2011 | Kang .................... G01J 3/4406 |
| | | 600/476 |
| 2011/0280810 A1 | 11/2011 | Hauger et al. |
| 2011/0295062 A1* | 12/2011 | Gratacos ............ A61B 5/0086 |
| | | 600/109 |
| 2012/0010465 A1 | 1/2012 | Erikawa et al. |
| 2012/0013773 A1 | 1/2012 | Yoshino et al. |
| 2012/0062722 A1 | 3/2012 | Sase |
| 2012/0108942 A1 | 5/2012 | Boutet et al. |
| 2012/0123205 A1 | 5/2012 | Nie et al. |
| 2012/0273470 A1 | 11/2012 | Zediker et al. |
| 2012/0294498 A1 | 11/2012 | Popovic |
| 2013/0070071 A1 | 3/2013 | Peltie et al. |
| 2013/0085484 A1 | 4/2013 | Van Valen et al. |
| 2013/0176395 A1 | 7/2013 | Kazakevich |
| 2013/0211246 A1 | 8/2013 | Parasher |
| 2013/0296710 A1 | 11/2013 | Zuzak et al. |
| 2013/0314520 A1 | 11/2013 | Ishihara |
| 2013/0324797 A1 | 12/2013 | Igarashi et al. |
| 2014/0073885 A1 | 3/2014 | Frangioni |
| 2014/0111623 A1 | 4/2014 | Zhao et al. |
| 2014/0160259 A1 | 6/2014 | Blanquart et al. |
| 2014/0163319 A1 | 6/2014 | Blanquart et al. |
| 2014/0201666 A1 | 7/2014 | Bedikian et al. |
| 2014/0210973 A1 | 7/2014 | Takahashi |
| 2014/0267655 A1 | 9/2014 | Richardson et al. |
| 2014/0276093 A1 | 9/2014 | Zeien |
| 2014/0300750 A1* | 10/2014 | Nagamune ................ G01J 3/51 |
| | | 348/164 |
| 2014/0303504 A1 | 10/2014 | Stankovic |
| 2014/0336501 A1 | 11/2014 | Masumoto |
| 2015/0015692 A1 | 1/2015 | Smart |
| 2015/0051498 A1 | 2/2015 | Darty |
| 2015/0073209 A1 | 3/2015 | Ikeda |
| 2015/0141268 A1 | 5/2015 | Rothberg et al. |
| 2015/0201118 A1 | 7/2015 | Lee et al. |
| 2015/0223733 A1 | 8/2015 | Al-Alusi |
| 2015/0305604 A1 | 10/2015 | Melsky |
| 2015/0309284 A1 | 10/2015 | Kagawa et al. |
| 2015/0381909 A1* | 12/2015 | Butte ................ A61B 1/00045 |
| | | 250/578.1 |
| 2016/0006914 A1 | 1/2016 | Neumann |
| 2016/0042513 A1 | 2/2016 | Yudovsky |
| 2016/0062103 A1 | 3/2016 | Yang et al. |
| 2016/0100741 A1 | 4/2016 | Ono et al. |
| 2016/0183775 A1 | 6/2016 | Blanquart et al. |
| 2016/0195706 A1 | 7/2016 | Fujii |
| 2016/0335778 A1 | 11/2016 | Smits |
| 2017/0017069 A1 | 1/2017 | Siegel et al. |
| 2017/0059305 A1 | 3/2017 | Nonn et al. |
| 2017/0086940 A1 | 3/2017 | Nakamura |
| 2017/0142312 A1* | 5/2017 | Dal Mutto .............. G06T 7/285 |
| 2017/0163971 A1 | 6/2017 | Wang et al. |

(56) References Cited

U.S. PATENT DOCUMENTS

| | | |
|---|---|---|
| 2017/0167980 A1 | 6/2017 | Dimitriadis et al. |
| 2017/0202461 A1 | 7/2017 | Darty et al. |
| 2017/0205198 A1 | 7/2017 | Roncone et al. |
| 2017/0209050 A1 | 7/2017 | Fengler et al. |
| 2017/0232269 A1 | 8/2017 | Luttrull et al. |
| 2017/0237958 A1 | 8/2017 | Themelis |
| 2017/0280029 A1 | 9/2017 | Steiner |
| 2017/0280970 A1 | 10/2017 | Sartor et al. |
| 2017/0293134 A1 | 10/2017 | Otterstrom et al. |
| 2017/0295325 A1 | 10/2017 | Yoon et al. |
| 2017/0360275 A1 | 12/2017 | Yoshizaki |
| 2017/0374281 A1 | 12/2017 | Kim et al. |
| 2018/0000401 A1 | 1/2018 | Kang et al. |
| 2018/0008138 A1 | 1/2018 | Thommen et al. |
| 2018/0014000 A1 | 1/2018 | Blanquart et al. |
| 2018/0020920 A1 | 1/2018 | Ermilov et al. |
| 2018/0020932 A1* | 1/2018 | Chen ............... A61B 5/0261 600/479 |
| 2018/0038845 A1 | 2/2018 | Zimmermann et al. |
| 2018/0234603 A1 | 7/2018 | Moore et al. |
| 2018/0217262 A1 | 8/2018 | Albelo et al. |
| 2018/0246313 A1 | 8/2018 | Eshel et al. |
| 2018/0270474 A1 | 9/2018 | Liu |
| 2018/0338802 A1 | 11/2018 | Wade |
| 2019/0125458 A1 | 5/2019 | Shelton, IV et al. |
| 2019/0129026 A1 | 5/2019 | Sumi et al. |
| 2019/0129037 A1 | 5/2019 | Fujita et al. |
| 2019/0191974 A1 | 6/2019 | Talbert et al. |
| 2019/0191975 A1 | 6/2019 | Talbert et al. |
| 2019/0191976 A1 | 6/2019 | Talbert et al. |
| 2019/0191977 A1 | 6/2019 | Talbert et al. |
| 2019/0191978 A1 | 6/2019 | Talbert et al. |
| 2019/0197712 A1 | 6/2019 | Talbert et al. |
| 2019/0200848 A1 | 7/2019 | McDowall et al. |
| 2020/0043160 A1 | 2/2020 | Mizukura et al. |
| 2020/0098104 A1 | 3/2020 | Kashima et al. |
| 2020/0397242 A1 | 12/2020 | Talbert et al. |
| 2020/0400500 A1 | 12/2020 | Talbert et al. |
| 2020/0400570 A1 | 12/2020 | Talbert et al. |
| 2020/0402207 A1 | 12/2020 | Talbert et al. |
| 2020/0402208 A1 | 12/2020 | Talbert et al. |
| 2020/0402209 A1 | 12/2020 | Talbert et al. |
| 2020/0402210 A1 | 12/2020 | Talbert et al. |
| 2020/0404171 A1 | 12/2020 | Talbert et al. |
| 2021/0356757 A1 | 11/2021 | Weigel et al. |
| 2022/0334061 A1 | 10/2022 | Talbert et al. |

FOREIGN PATENT DOCUMENTS

| | | |
|---|---|---|
| JP | 2002315721 A | 10/2002 |
| JP | 2008259595 A | 10/2008 |
| JP | 2010125284 A | 6/2010 |
| JP | 2011206227 A | 10/2011 |
| JP | 2012016545 A | 1/2012 |
| JP | 2012019982 A | 2/2012 |
| JP | 2012105715 A | 6/2012 |
| JP | 2012213550 A | 11/2012 |
| JP | 2015119836 A | 7/2015 |
| JP | 2016007336 A | 1/2016 |
| JP | 2016202726 A | 12/2016 |
| JP | 2018042676 A | 3/2018 |
| WO | 2014018951 A1 | 1/2014 |
| WO | 2014134314 A1 | 9/2014 |
| WO | WO 2015077493 A1 | 5/2015 |
| WO | WO 2014073138 A1 | 9/2016 |
| WO | 2016203572 A1 | 12/2016 |
| WO | WO 2017201093 A1 | 11/2017 |
| WO | WO 2018049215 A1 | 3/2018 |
| WO | WO 2019133736 A1 | 7/2019 |
| WO | WO 2019133737 A1 | 7/2019 |
| WO | WO 2019133739 A1 | 7/2019 |
| WO | WO 2019133741 A1 | 7/2019 |
| WO | WO 2019133750 A1 | 7/2019 |
| WO | WO 2019133753 A1 | 7/2019 |
| WO | 2020256954 A1 | 12/2020 |
| WO | 2020256955 A1 | 12/2020 |
| WO | 2020256956 A1 | 12/2020 |
| WO | 2020256957 A1 | 12/2020 |
| WO | 2020256958 A1 | 12/2020 |

OTHER PUBLICATIONS

USPTO, Written Opinion for PCT/US2020/36152 (Year: 2020).*
English Translation of JP2008259595 prepared by Google Patents (https://patents.google.com/patent/JP2008259595A/en?oq=JP2008259595).
English Translation of WO2016203572 prepared by Google Patents (https://patents.google.com/patent/WO2016203572A1/en?oq=WO2016203572).
English Translation of CN111526775A prepared by Google Patents (https://patents.google.com/patent/CN111526775N/en?oq=CN111526775).
English Translation of JP H04-158205 prepared by Google Patents (https://patents.google.com/patent/JPH04158205A/en?oq=JPH04158205).
English Translation of JP2002315721 prepared by Google Patents (https://patents.google.com/patent/JP2002315721A/en?oq=JP2002315721).
English Translation of JP2010125284 prepared by Google Patents (https://patents.google.com/patent/JP2010125284A/en?oq=JP2010125284).
English Translation of JP 2011206227 prepared by Google Patents (https://patents.google.com/patent/JP2011206227A/en?oq=JP2011206227).
English Translation of JP 2012016545 prepared by Google Patents (https://patents.google.com/patent/JP2012016545A/en?oq=JP2012016545).
English Translation of JP 2012105715 prepared by Google Patents (https://patents.google.com/patent/JP2012105715A/en?oq=JP2012105715).
English Translation of JP2012213550 prepared by Google Patents (https://patents.google.com/patent/JP2012213550A/en?oq=2012213550).
English Translation of JP2016007336 prepared by Google Patents (https://patents.google.com/patent/JP2016007336A/en?oq=JP2016007336).
English Translation of JP2018042676 prepared by Google Patents (https://patents.google.com/patent/JP2018042676A/en?oq=JP2018042676).
English Translation of WO2014073138 prepared by Google Patents (https://patents.google.com/patent/JPWO2014073138A1/en?oq=WO2014073138).
English Translation of Notification of Reasons for Refusal issued by the Japanese Intellectual Property Office dated Dec. 6, 2022, in connection with Japanese Patent Application No. 2020-536245.
English Translation of Notification of Reasons for Refusal issued by the Japanese Intellectual Property Office dated Dec. 6, 2022, in connection with Japanese Patent Application No. 2020-536038.
English Translation of Notification of Reasons for Refusal issued by the Japanese Intellectual Property Office dated Dec. 6, 2022, in connection with Japanese Patent Application No. 2020-536243.

* cited by examiner

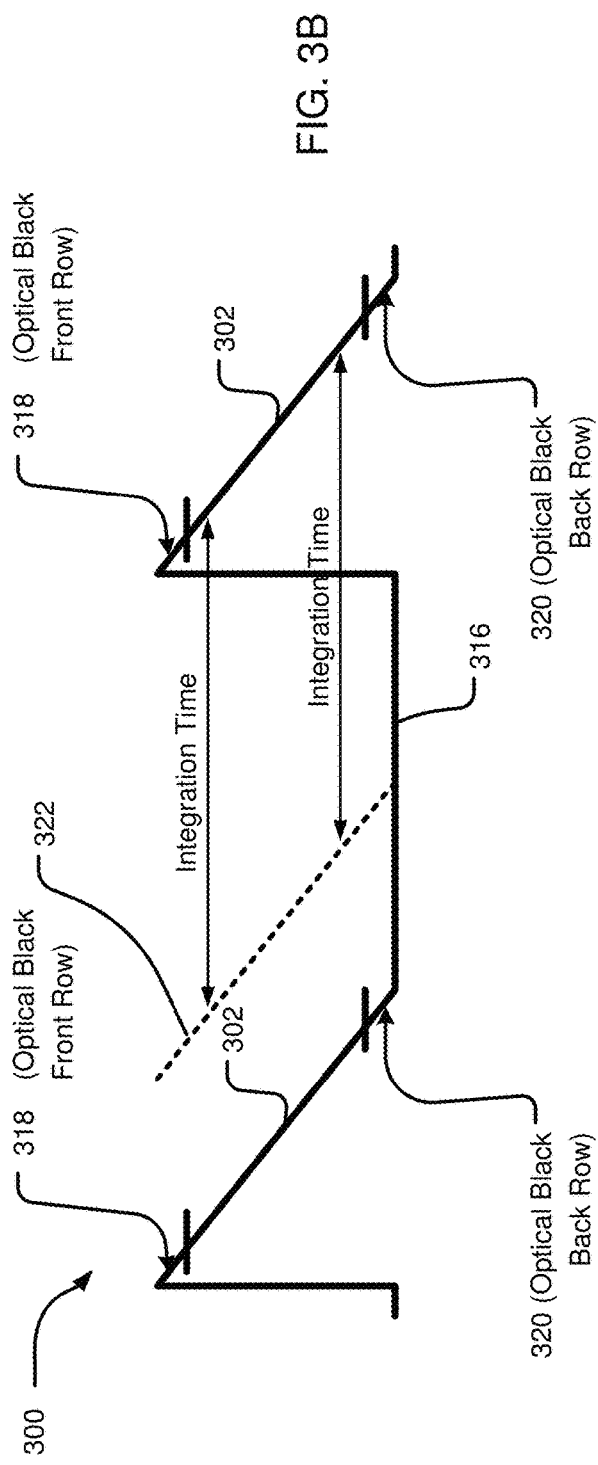
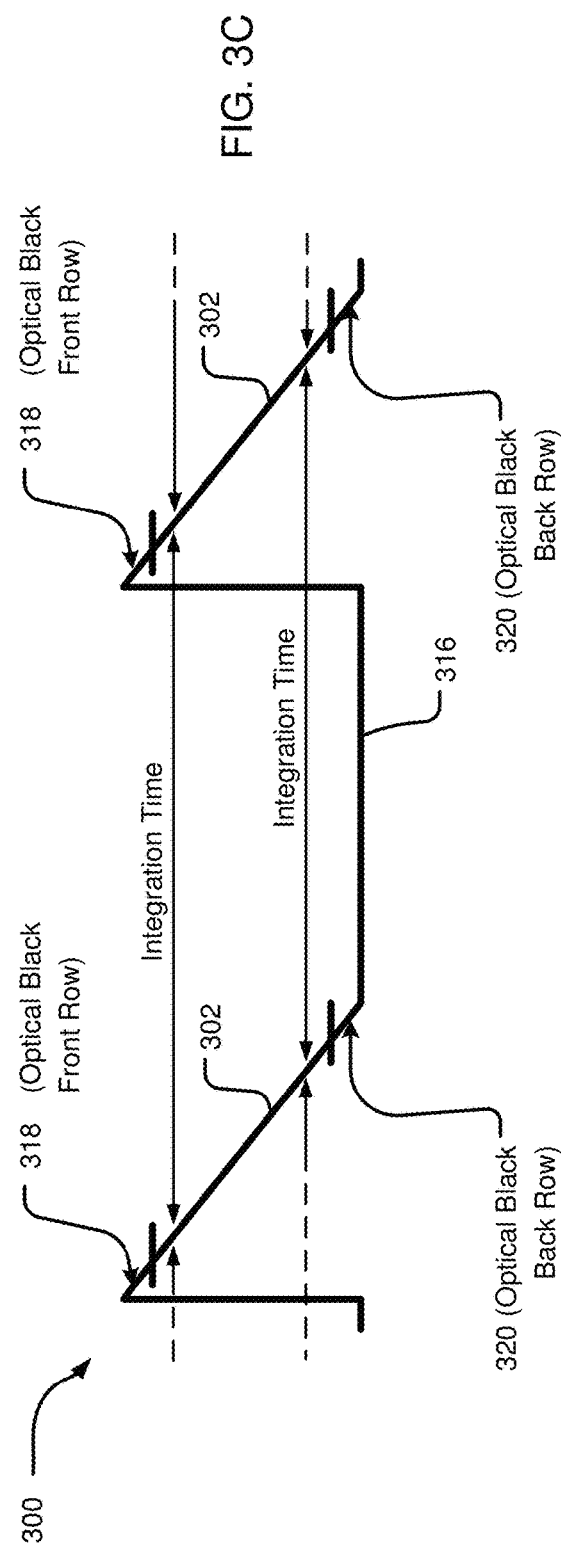

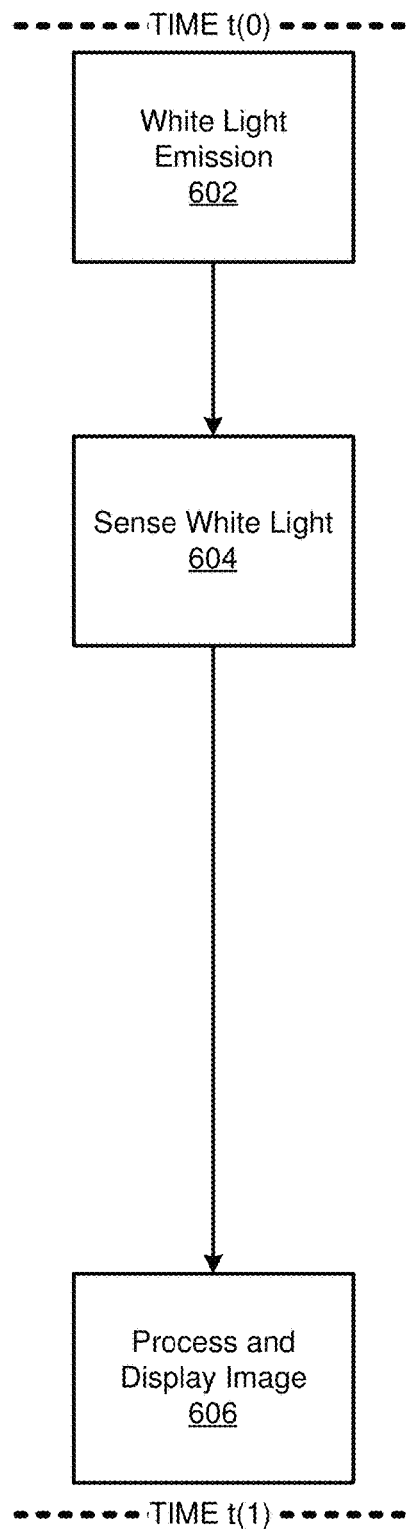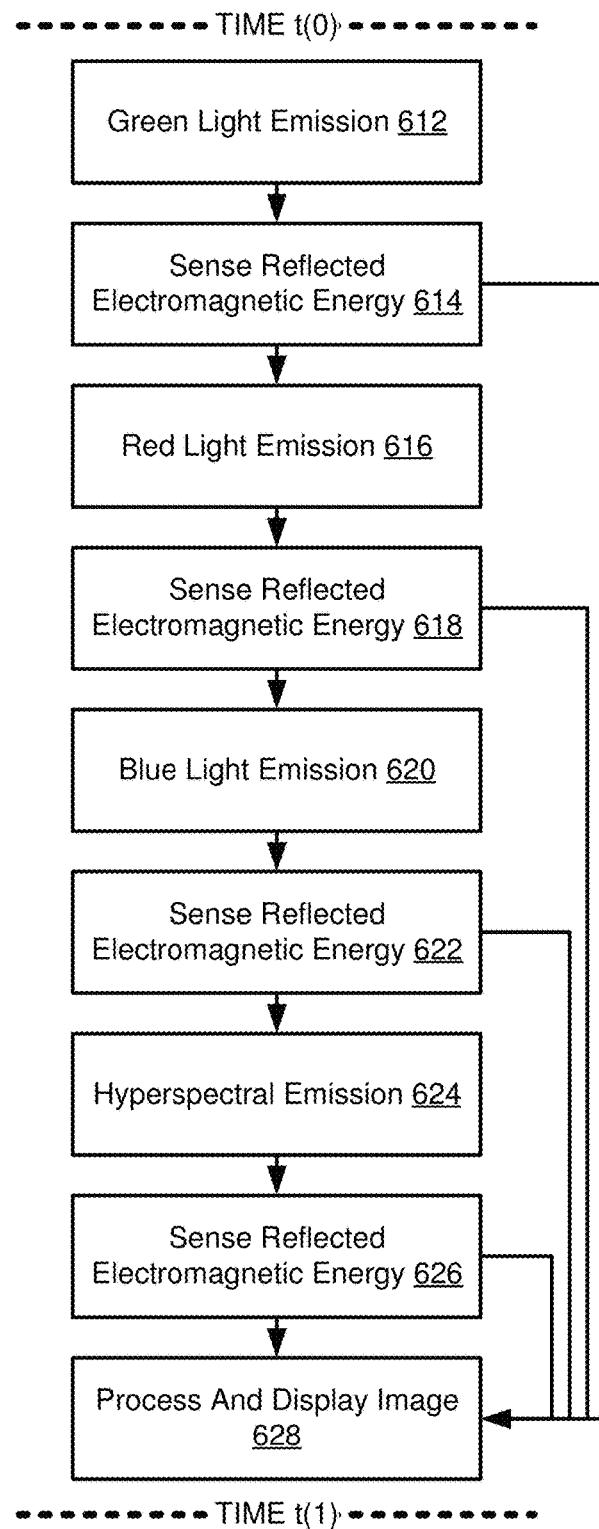
FIG. 6A
(Prior Art)
FIG. 6B 3D with double pixel array

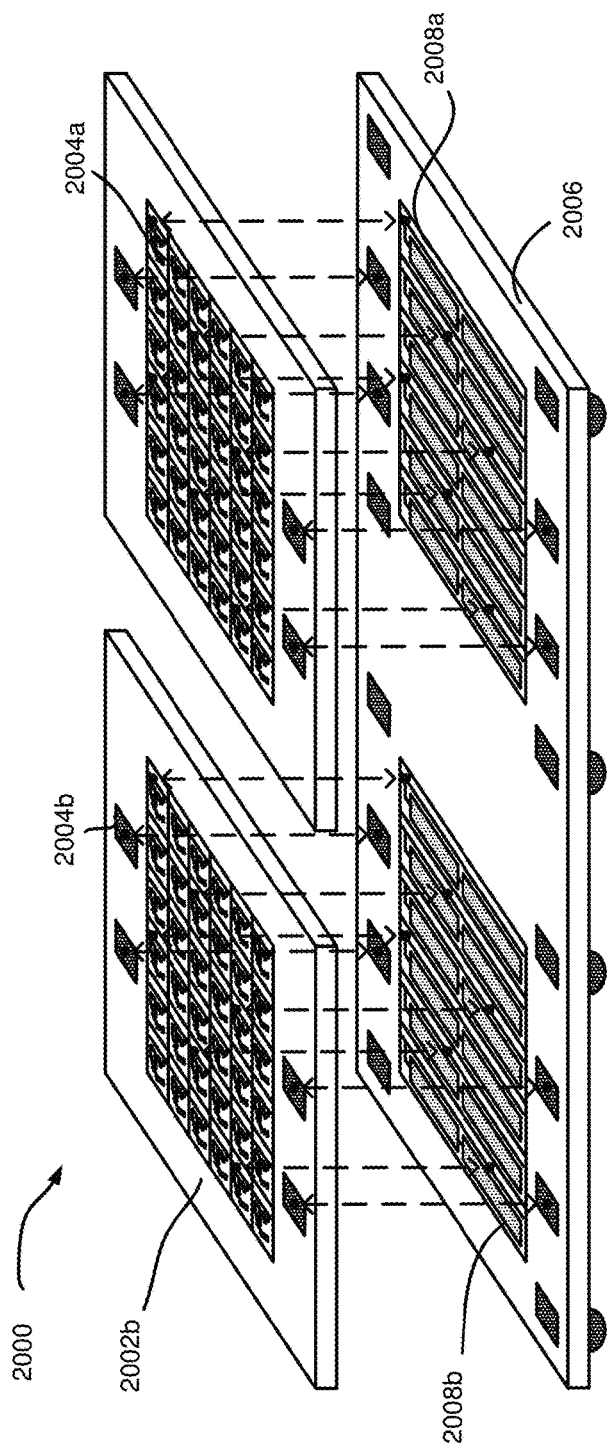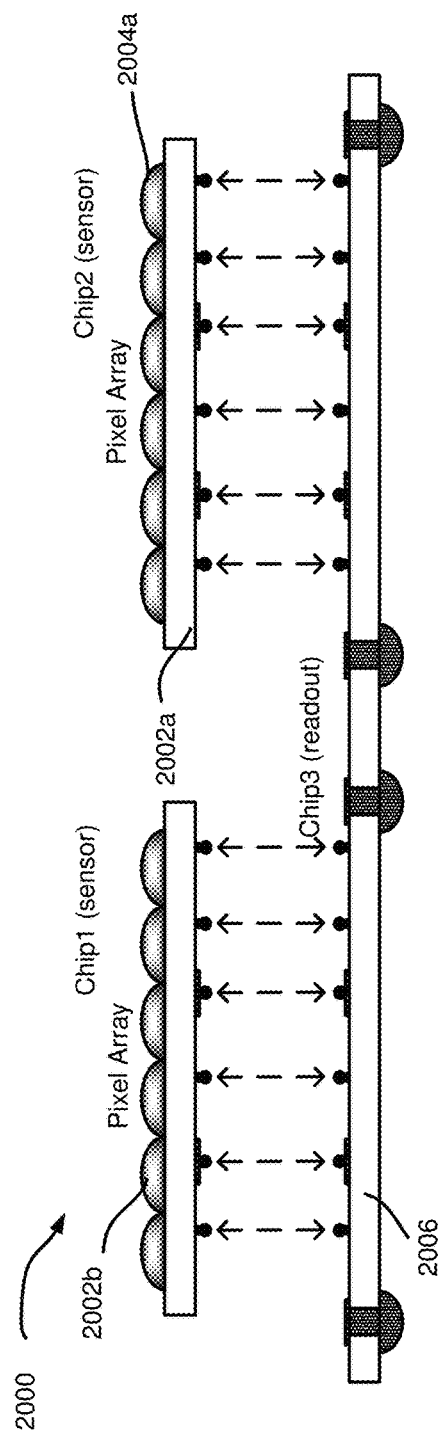
FIG. 20A
FIG. 20B

SUPER RESOLUTION AND COLOR MOTION ARTIFACT CORRECTION IN A PULSED HYPERSPECTRAL IMAGING SYSTEM

CROSS-REFERENCE TO RELATED APPLICATIONS

This application claims the benefit of U.S. Provisional Patent Application No. 62/864,213, filed Jun. 20, 2019, titled "SUPER RESOLUTION AND COLOR MOTION ARTIFACT CORRECTION IN A PULSED HYPERSPECTRAL AND FLUORESCENCE IMAGING SYSTEM," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This application is directed to digital imaging and is particularly directed to hyperspectral imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with hyperspectral image data in addition to color image data. Color images reflect what the human eye detects when looking at an environment. However, the human eye is limited to viewing only visible light and cannot detect other wavelengths of the electromagnetic spectrum. At other wavelengths of the electromagnetic spectrum beyond the "visible light" wavelengths, additional information may be obtained about an environment. One means for obtaining image data outside the visible light spectrum is the application of hyperspectral imaging.

Hyperspectral imaging is used to identify different materials or objects and to identify different processes by providing information beyond what is visible to the human eye. Unlike a normal camera image that provides limited information to the human eye, hyperspectral imaging can identify specific compounds and biological processes based on the unique spectral signatures of the compounds and biological processes. Hyperspectral imaging is complex and requires fast computer processing capacity, sensitive detectors, and large data storage capacities.

Hyperspectral imaging traditionally requires specialized image sensors that consume significant physical space and cannot fit within the distal end of an endoscope. Further, if a hyperspectral image is overlaid on a black-and-white or color image to provide context to a practitioner, a camera (or multiples cameras) capable of generating the overlaid image may have many distinct types of pixel sensors that are sensitive to distinct ranges of electromagnetic radiation. This would include the three separate types of pixels sensors for generating an RGB color image along with additional pixel sensors for generating the hyperspectral image data at different wavelengths of the electromagnetic spectrum. This consumes significant physical space and necessitates a large pixel array to ensure the image resolution is satisfactory. In the case of endoscopic imaging, the camera or cameras would be too large to be placed at the distal end of the endoscope and may therefore be placed in an endoscope hand unit or robotic unit. This introduces the same disadvantages mentioned above and can cause the endoscope to be very delicate such that image quality is significantly degraded when the endoscope is bumped or impacted during use.

In light of the foregoing, described herein are improved systems, methods, and devices for endoscopic imaging in a light deficient environment. The systems, methods, and devices disclosed herein provide means for color and hyperspectral imaging with an endoscopic device.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where:

FIGS. 3A to 3D are illustrations of the operational cycles of an image sensor used to construct one or more exposure frames;

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIGS. 20A and 20B illustrate a perspective view and a side view, respectively, of an implementation of an imaging sensor having a plurality of pixel arrays for producing a three-dimensional image, wherein the plurality of pixel arrays and the image sensor are built on a plurality of substrates.

DETAILED DESCRIPTION

Figure 1:
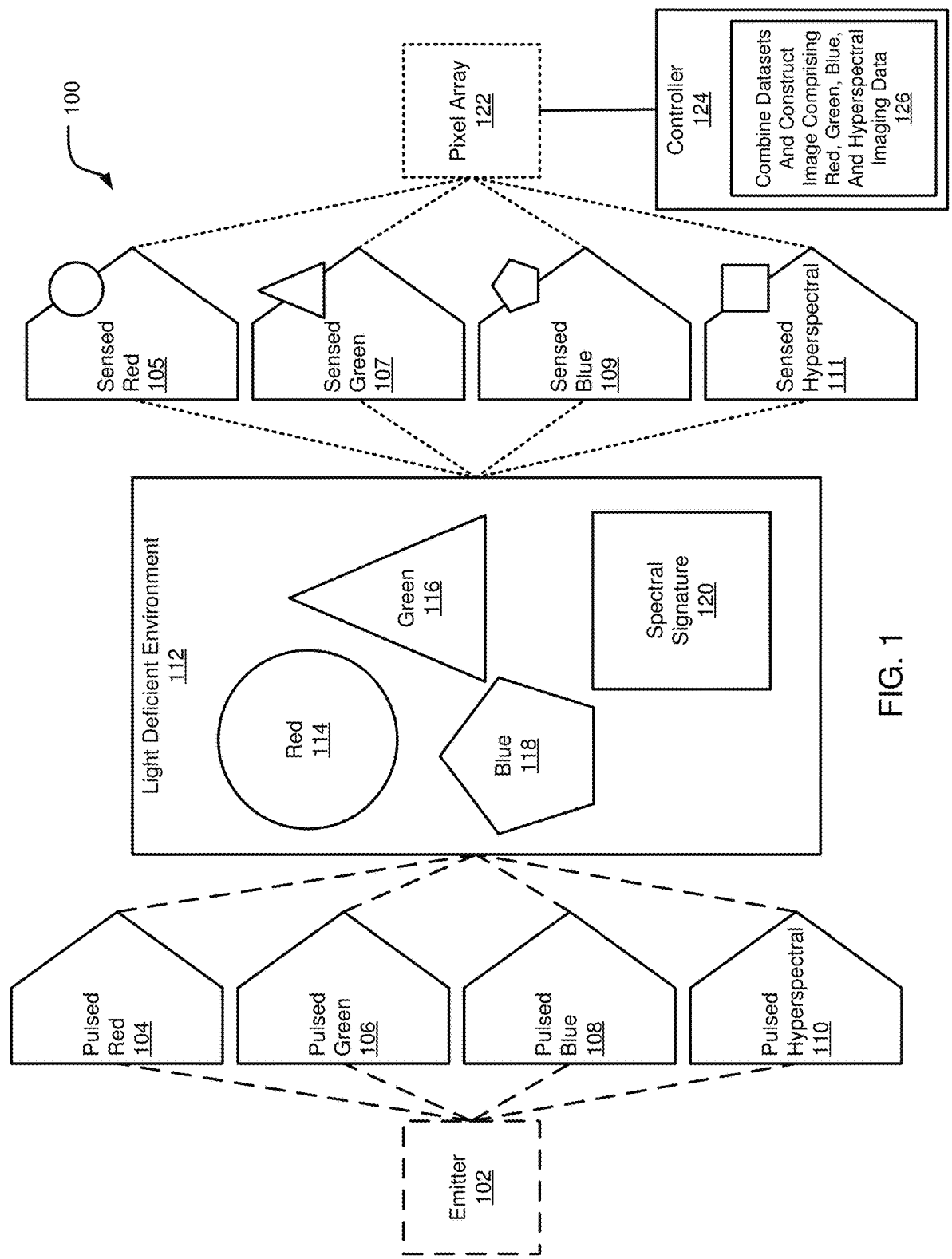
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for hyperspectral and/or color imaging in a light deficient environment.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within a distal end of the endoscope itself. This provides greater optical simplicity when compared with implementations known in the art. However, an acceptable solution to this approach is by no means trivial and introduces its own set of engineering challenges, not least of which that the image sensor must fit within a highly constrained area.

The imaging systems disclosed herein place aggressive constraints on the size of the image sensor. This enables the image sensor to be placed in a distal end of an endoscope and thereby enables the corresponding benefits of improved optical simplicity and increased mechanical robustness for the endoscope. However, placing these aggressive constraints on the image sensor area results in fewer and/or smaller pixels and can degrade image quality. An embodiment of the disclosure overcomes this challenge by incorporating a monochrome image sensor with minimal peripheral circuitry, connection pads, and logic. The imaging systems disclosed herein provide means for extending the dynamic range, sensor sensitivity, and spatial resolution of resultant images while still decreasing the overall size of the image sensor through the application of super resolution and color motion artifact correction algorithms.

In an embodiment, the super resolution algorithm is deployed to enhance perceived resolution of an image and extract motion information from a series of sequential exposure frames that are captured sequentially in time. Each of the sequential exposure frames is generated by a pixel array of an image sensor. The pixel array senses reflected electromagnetic radiation from a pulse of electromagnetic radiation that is emitted by an emitter. The pulses of electromagnetic radiation may include red, green, blue, and/or hyperspectral pulses for generating red exposure frames, green exposure frames, blue exposure frames, and/or hyperspectral exposure frames. A grouping of sequential exposure frames are combined to generate an image frame with increased spatial resolution when compared with the individual exposure frames. The super resolution algorithm and the color motion artifact correction processes disclosed herein detect motion in a scene, correct for the detected motion, and increase spatial resolution of a resultant image frame by combining multiple exposure frames.

For digital imaging systems, the final quality of a video stream depends on engineering details of the electronic capture process deployed by the image sensor. The perceived quality of an image frame is dependent on, among other things, the signal to noise ratio (SNR), the dynamic range (DR), the spatial resolution, the perception of visible unnatural artifacts, the perception of spatial distortion, and the color fidelity and appeal of the image frame. Each of these factors can be negatively impacted by decreasing the overall size of the image sensor. Therefore, in an effort to increase the perceived quality of a resultant image frame, traditional cameras known in the art include multiple image sensors or include an enlarged image sensor. For example, high-end cameras that can produce high resolution images typically include at least three monochrome sensors that are precisely coupled in an elaborate arrangement of prisms and filters. Another traditional solution is to use a single sensor with individual pixel-sized color filters fabricated on to the image sensor in a mosaic arrangement. The most popular mosaic arrangement is the Bayer pattern. An image sensor with a Bayer pattern can be inexpensive to fabricate but cannot achieve the image quality realized by the three-image sensor solution implemented in high-end cameras. An additional undesirable side effect of the Bayer pattern is that the color segmentation pattern introduces artifacts in the resultant image frames, and these artifacts can be especially noticeable around black and white edges.

One traditional approach to decreasing the size of the image sensor is to increase the number of pixels in the pixel array and reduce the size of the individual pixels. However, smaller pixels naturally have lower signal capacity. The lower signal capacity reduces the dynamic range of data captured by the pixels and reduces the maximum possible signal to noise ratio. Decreasing the area of an individual pixel reduces the sensitivity of the pixel not only in proportion with the capture area of the pixel but to a greater degree. The loss of sensitivity for the pixel may be compensated by widening the aperture, but this leads to a shallower depth of field and shallower depth of focus. The shallower depth of field impacts the resolution of the resultant image and can lead to greater spatial distortion. Additionally, smaller pixels are more challenging to manufacture consistently, and this may result in greater defect rates.

In light of the deficiencies associated with decreasing the capture area of the pixels, disclosed herein are systems, methods, and devices for reducing pixel count and bolstering image resolution by other means. In an embodiment, a monochrome image sensor is used with "color agnostic" pixels in the pixel array. The color information is determined by capturing independent exposure frames in response to pulses of different wavelengths of electromagnetic radiation. The alternative pulses may include red, green, and blue wavelengths for generating an RGB image frame consisting of a red exposure frame, a green exposure frame, and a blue exposure frame. The image frame may further include data from a hyperspectral exposure frame overlaid on the RGB image frame. The hyperspectral pulse may include one or more pulses of electromagnetic radiation for eliciting a spectral response. In an embodiment, the hyperspectral emission includes one or more of electromagnetic radiation having a wavelength from about 513 nm to about 545 nm; from about 565 nm to about 585 nm; or from about 900 nm to about 1000 nm. Alternating the wavelengths of the pulsed electromagnetic radiation allows the full pixel array to be exploited and avoids the artifacts introduced by Bayer pattern pixel arrays.

In an embodiment, each pulse or grouping of pulses of electromagnetic radiation results in an exposure frame sensed by the pixel array. A plurality of exposure frames may be combined to generate an image frame. The image frame may include, for example, a red exposure frame generated in response to a red pulse, a green exposure frame generated in response to a green pulse, a blue exposure frame generated in response to a blue pulse, and a hyperspectral exposure frame generated in response to a hyperspectral pulse. The red, green, blue, and hyperspectral exposure frames can be combined to generate a single RGB image frame with hyperspectral data overlaid thereon. This method results in increased dynamic range and spatial resolution in the resultant image frame. However, this method can introduce motion blur because the multiple exposure frames making up the image frame are captured over time. Additionally, because the independent exposure frames supply different color components, the image frame can have unnatural colored effects that may be particularly visible in the vicinity of large edges. In light of the foregoing, the systems, methods, and devices disclosed herein correct for motion introduced by frame-wise color switching.

In some instances, it is desirable to generate endoscopic imaging with multiple data types or multiple images overlaid on one another. For example, it may be desirable to generate an RGB image frame that further includes hyperspectral imaging data overlaid on the RGB image frame. An overlaid image of this nature may enable a medical practitioner or computer program to identify critical body structures based on the hyperspectral imaging data. Historically, this would require the use of multiple sensor systems including an image sensor for color imaging and one or more additional image sensors for hyperspectral imaging. In such systems, the multiple image sensors would have multiple types of pixel sensors that are each sensitive to distinct ranges of electromagnetic radiation. In systems known in the art, this includes the three separate types of pixel sensors for generating an RGB color image along with additional pixel sensors for generating the hyperspectral image data at different wavelengths of the electromagnetic spectrum. Traditionally, these multiple different pixel arrays consume a prohibitively large physical space and cannot be located at a distal tip of the endoscope. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Hyperspectral Imaging

In an embodiment, the systems, methods, and devices disclosed herein provide means for generating hyperspectral imaging data in a light deficient environment. Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any band of wavelengths in the electromagnetic spectrum, including infrared wavelengths, the visible spectrum, the ultraviolet spectrum, x-ray wavelengths, or any suitable combination of various wavelength bands.

Hyperspectral imaging was originally developed for applications in mining and geology. Unlike a normal camera image that provides limited information to the human eye, hyperspectral imaging can identify specific minerals based on the spectral signatures of the different minerals. Hyperspectral imaging can be useful even when captured in aerial images and can provide information about, for example, oil or gas leakages from pipelines or natural wells and their effects on nearby vegetation. This information is collected based on the spectral signatures of certain materials, objects, or processes that may be identified by hyperspectral imaging. Hyperspectral imaging is also useful in medical imaging applications where certain tissues, chemical processes, biological processes, and diseases can be identified based on unique spectral signatures.

In an embodiment of hyperspectral imaging, a complete spectrum or some spectral information is collected at every pixel in an image plane. A hyperspectral camera may use special hardware to capture any suitable number of wavelength bands for each pixel which may be interpreted as a complete spectrum. The goal of hyperspectral imaging varies for different applications. In one application, the goal is to obtain imaging data for the entire electromagnetic spectrum for each pixel in an image scene. In another application, the goal is to obtain imaging data for certain partitions of the electromagnetic spectrum for each pixel in an image scene. The certain partitions of the electromagnetic spectrum may be selected based on what might be identified in the image scene. These applications enable certain materials, tissues, chemical processes, biological processes, and diseases to be identified with precision when those materials or tissues might not be identifiable under the visible light wavelength bands. In some medical applications, hyperspectral imaging includes one or more specific partitions of the electromagnetic spectrum that have been selected to identify certain tissues, diseases, chemical processes, and so forth. Some example partitions of the electromagnetic spectrum that may be pulsed for hyperspectral imaging in a medical application include electromagnetic radiation having a wavelength from about 513 nm to about 545 nm; from about 565 nm to about 585 nm; and/or from about 900 nm to about 1000 nm. It should be appreciated that different partitions of electromagnetic radiation may be pulsed to elicit a spectral response from a material for generating a hyperspectral exposure frame. In an embodiment, a hyperspectral exposure frame is generated in response to pulsing electromagnetic radiation having a wavelength from about 513 nm to about 545 nm and electromagnetic radiation having a wavelength from about 900 nm to about 1000 nm. In a further embodiment, a hyperspectral exposure frame is generated in response to pulsing electromagnetic radiation having a wavelength from about 565 nm to about 585 nm and electromagnetic radiation having a wavelength from about 900 nm to about 1000 nm.

Hyperspectral imaging enables numerous advantages over conventional imaging and enables particular advantages in medical applications. Endoscopic hyperspectral imaging permits a health practitioner or computer-implemented program to identify nervous tissue, muscle tissue, vessels, cancerous cells, typical non-cancerous cells, the direction of blood flow, and more. Hyperspectral imaging enables atypical cancerous tissue to be precisely differentiated from typical healthy tissue and may therefore enable a practitioner or computer-implemented program to discern the boundary of a cancerous tumor during an operation or investigative imaging. The information obtained by hyperspectral imaging enables the precise identification of certain tissues or conditions that may lead to diagnoses that may not be possible or may be less accurate if using conventional imaging. Additionally, hyperspectral imaging may be used during medical procedures to provide image-guided surgery that enables a medical practitioner to, for example, view tissues located behind certain tissues or fluids, identify atypical cancerous cells in contrast with typical healthy cells, identify certain tissues or conditions, identify critical structures, and so forth. Hyperspectral imaging provides specialized diagnostic information about tissue physiology, morphology, and composition that cannot be generated with conventional imaging. Information gathered from hyperspectral imaging can be leveraged for robotic surgical procedures that may be performed with human supervision or without any human intervention.

In an embodiment of the disclosure, an endoscopic system illuminates a source and pulses electromagnetic radiation for spectral or hyperspectral imaging. The pulsed hyperspectral imaging discussed herein includes pulsing one or more bands of the electromagnetic spectrum, and may include infrared wavelengths, the visible spectrum, the ultraviolet spectrum, x-ray wavelengths, or any suitable combination of various wavelength bands. In an embodiment, hyperspectral imaging includes pulsing electromagnetic radiation having a wavelength from about 513 nm to about 545 nm; from about 565 nm to about 585 nm; and/or from about 900 nm to about 1000 nm.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral image. The pixels may be color agnostic such that each pixel generates data for each pulse of electromagnetic radiation, including pulses for red, green, and blue visible light wavelengths along with other wavelengths used for hyperspectral imaging.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Because the pixels are color agnostic, the effective spatial resolution is appreciably higher than for color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with hyperspectral data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in an exposure frame comprising image data sensed by the pixel array 122.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108 wavelengths, and a hyperspectral 110 emission. The hyperspectral 110 emission may include a band of wavelengths in the electromagnetic spectrum that elicit a spectral response. The hyperspectral 110 emission may include multiple separate emissions that are separate and independent from one another.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. This data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. This data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. This data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting a hyperspectral 110 emission for identifying elements sensitive to hyperspectral radiation that emit a spectral signature 120. The emitter 102 is capable of emitting the pulsed red 104, pulsed green 106, pulsed blue 108, and pulsed hyperspectral 110 emissions in any desired sequence.

The pixel array 122 senses reflected electromagnetic radiation. Each of the sensed red 105, the sensed green 107, the sensed blue 109, and the sensed hyperspectral 111 data can be referred to as an "exposure frame." The sensed hyperspectral 111 may result in multiple separate exposure frames that are separate and independent from one another. For example, the sensed hyperspectral 111 may result in a first hyperspectral exposure frame at a first partition of electromagnetic radiation, a second hyperspectral exposure frame at a second partition of electromagnetic radiation, and so forth. Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed hyperspectral 111 exposure frame identifying the spectral signatures 120 of elements sensitive to hyperspectral wavelengths of electromagnetic radiation and corresponding in time with the hyperspectral 110 emission.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, laser scanning data, fluorescence imaging data, and/or hyperspectral imaging data.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further identifies elements emitting a spectral signature 120 in response to a hyperspectral wavelength of electromagnetic radiation. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

In an embodiment, the red, green, and blue emissions are pulsed in combination. For every second frame, the relative energies of the red, green, and blue emissions are set in proportion to the standard luminance coefficients to provide direct luminance information. On alternate frames, the chrominance (Cb and Cr) information is determined by calculating a linear sum of the standard luminance and chrominance coefficients to adjust the corresponding individual pulse energies to zero or positive values. The chrominance frames may alternate between blue-difference chrominance (Cb) and red-difference chrominance (Cr) according to the Y-Cb-Y-Cr sequence. This approach results in increased perceived resolution when compared with pure red, green, and blue (R-G-B-G) pulsing because the luminance information per resolution output frame is derived from a single captured frame. With R-G-B-G pulsing, data from three sequential exposure frames are combined to provide the luminance information. Therefore, any motion in the scene or motion by the image sensor will impact the sharpness of the combined image frame.

Figure 2:
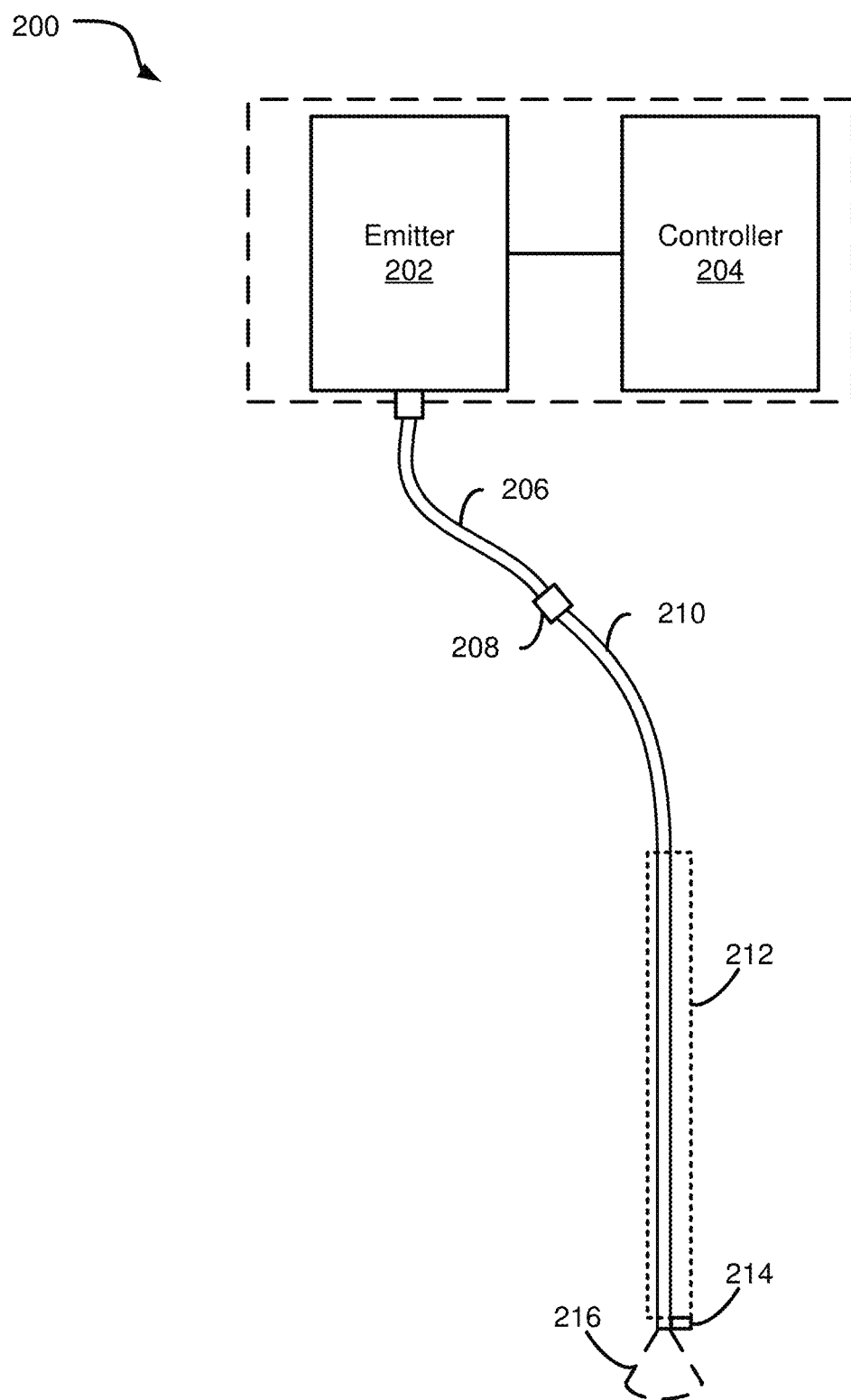
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, laser scanning pulsing schemes, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera control unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
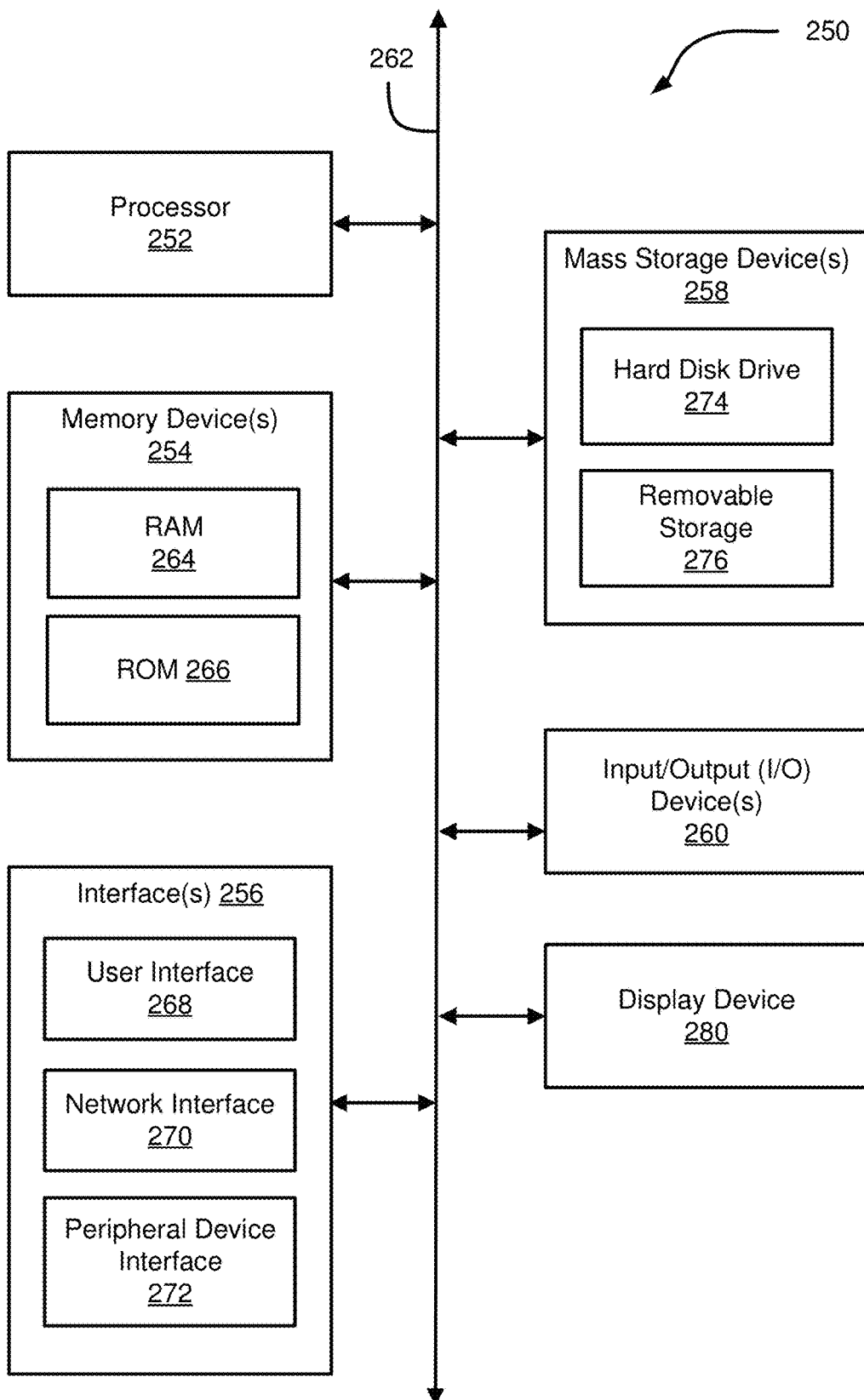
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera control unit, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
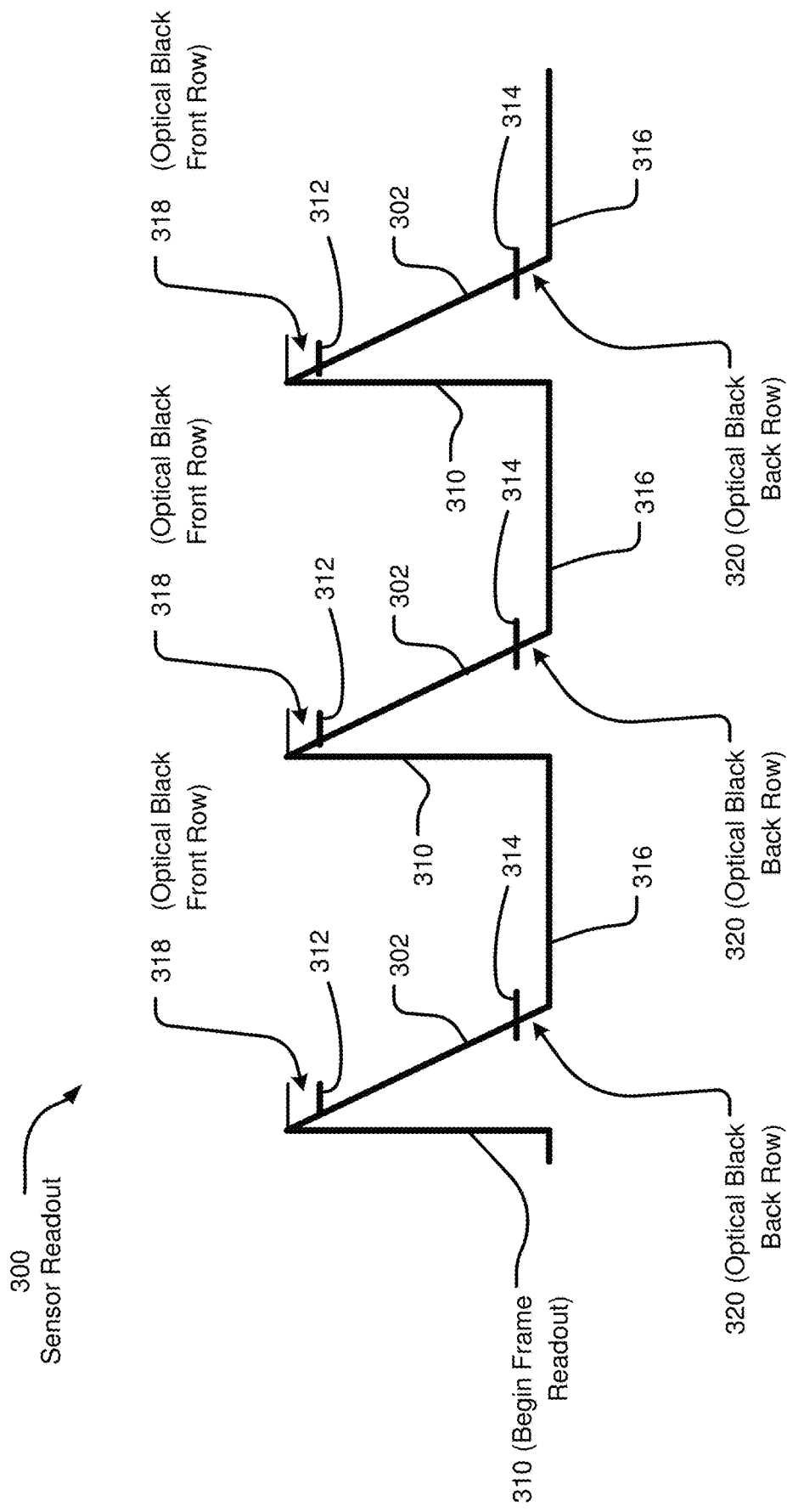

FIG. 3A illustrates the operational cycles of a sensor used in rolling readout mode or during the sensor readout 300. The frame readout period may start at and may be represented by vertical line 310. The readout period 302 is represented by the diagonal or slanted line. The sensor may be read out on a row by row basis, the top of the downwards slanted edge being the sensor top row 312 and the bottom of the downwards slanted edge being the sensor bottom row 314. The time between the last row readout and the next readout period may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout period. The position of the electronic shutter 322 can be moved between two readout periods 302 to control the pixel saturation for a given amount of light. It should be noted that this technique allows for a constant integration time between two different lines but introduces a delay when moving from top to bottom rows.

FIG. 3C illustrates the case where the electronic shutter 322 has been removed. In this configuration, the integration of the incoming light may start during the readout period 302 and may end at the next readout period 302, which also defines the start of the next integration.

Figure 3D:
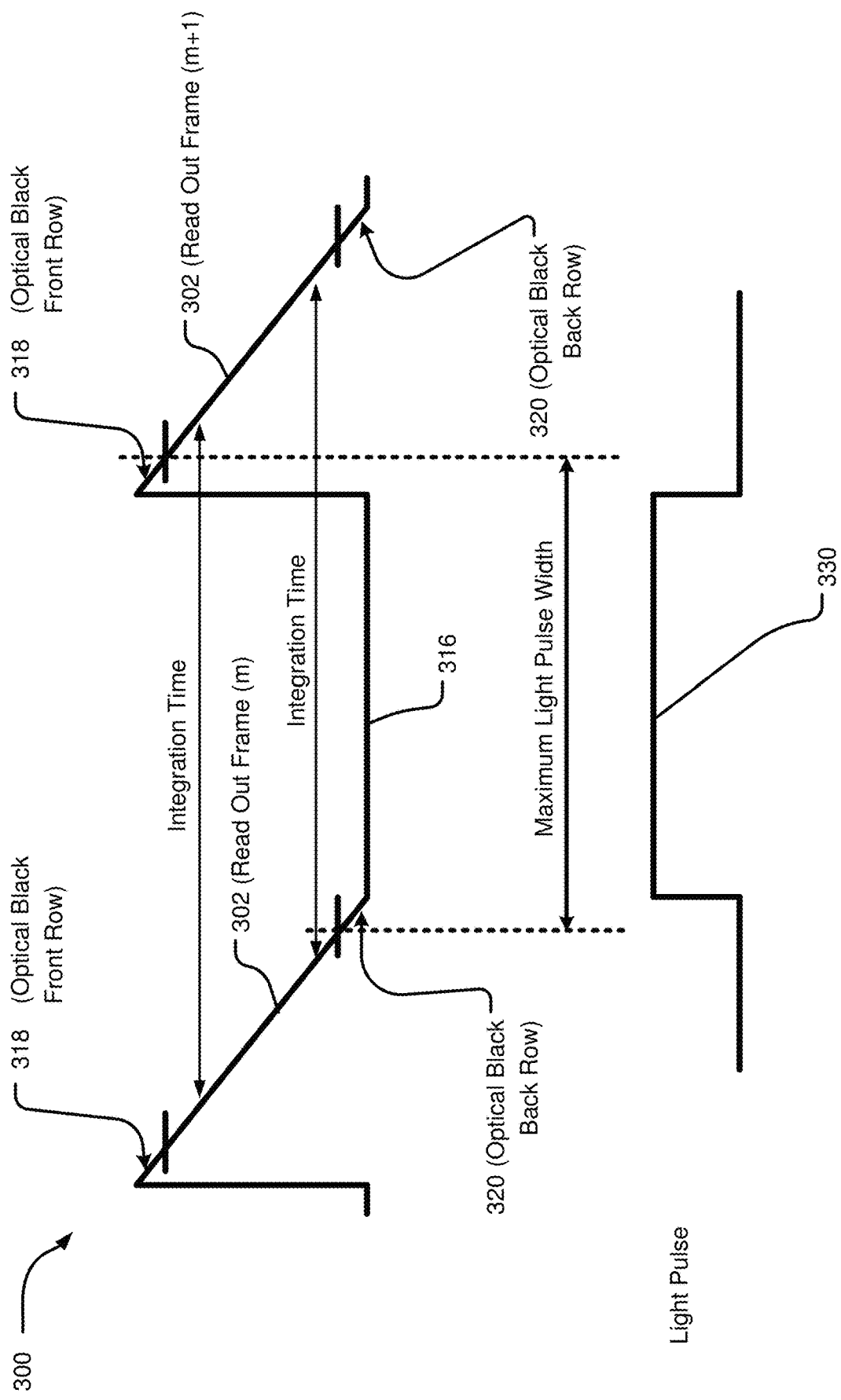

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
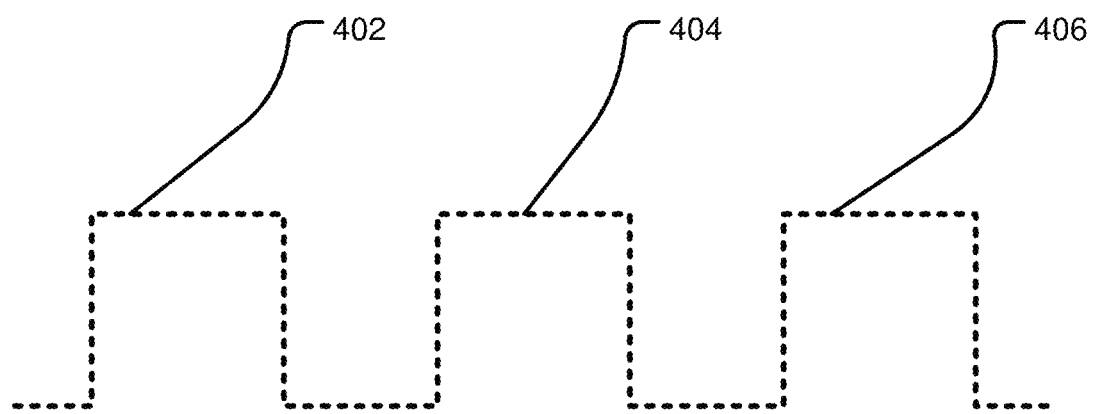
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking period 316 of the sensor operation cycle. In an embodiment, the emitter may pulse for a duration that is during portions of two or more sensor operational cycles. In an embodiment, the emitter may begin a pulse during the blanking period 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
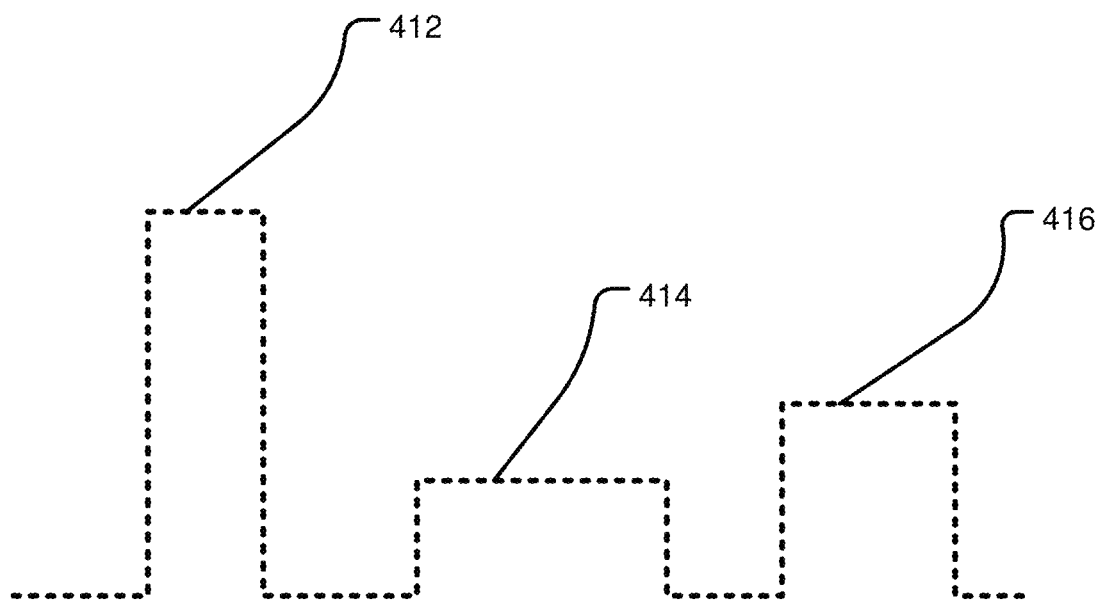
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
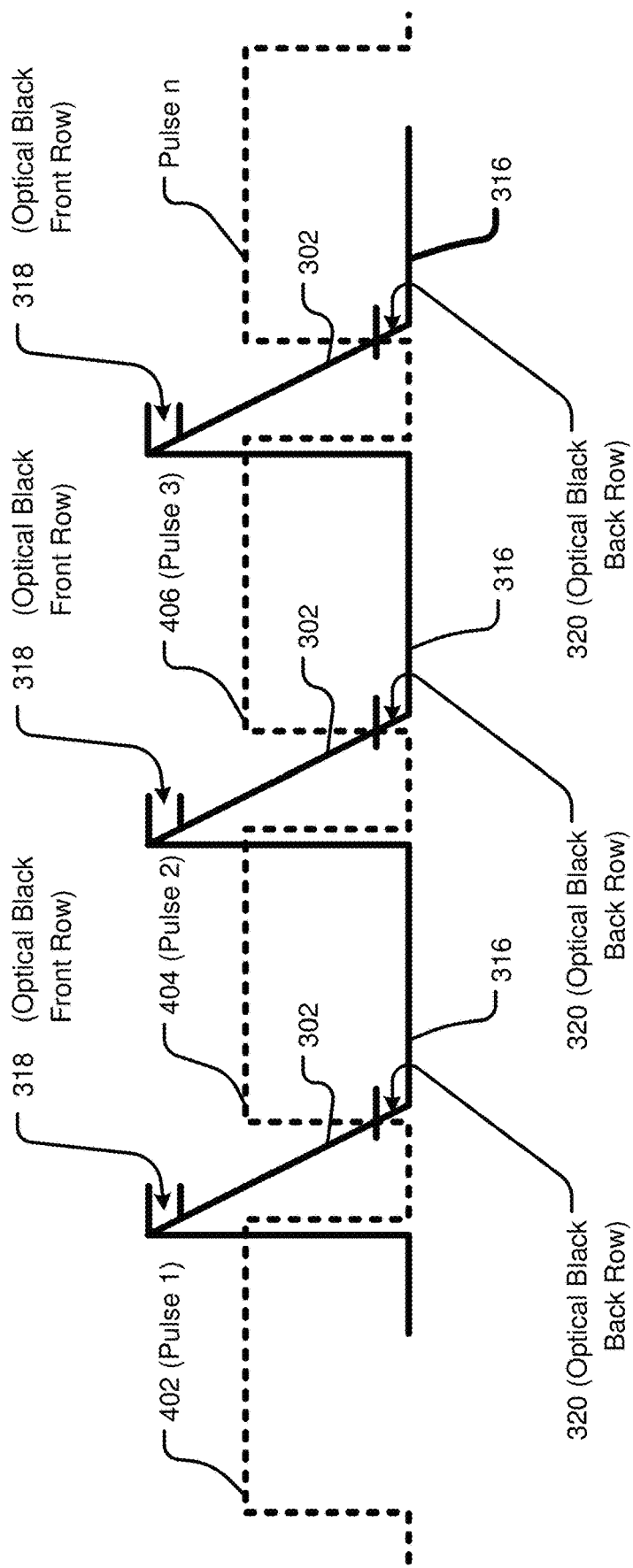
FIG. 5 is a graphical representation of an embodiment of the disclosure combining the operational cycles of an image sensor, an electromagnetic emitter, and the emitted electromagnetic pulses of FIGS. 3A-4A, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an RGB image frame is generated based on three exposure frames, including a red exposure frame generated by the image sensor subsequent to a red emission, a green exposure frame generated by the image sensor subsequent to a green emission, and a blue exposure frame generated by the image sensor subsequent to a blue emission. Hyperspectral imaging data may be overlaid on the RGB image frame. The hyperspectral imaging data may be drawn from one or more hyperspectral exposure frames. A hyperspectral exposure frame includes data generated by the image sensor during the readout period 302 subsequent to a hyperspectral emission of electromagnetic radiation. The hyperspectral emission includes any suitable emission in the electromagnetic spectrum and may include multiple emissions of light that span up to the entire electromagnetic spectrum. In an embodiment, the hyperspectral emission includes an emission of electromagnetic radiation having a wavelength from about 513 nm to about 545 nm; from about 565 nm to about 585 nm; and/or from about 900 nm to about 1000 nm. The hyperspectral exposure frame may include multiple hyperspectral exposure frames that are each generated by the image sensor subsequent to a different type of hyperspectral emission. In an embodiment, the hyperspectral exposure frame includes multiple hyperspectral exposure frames, such as a hyperspectral exposure frame generated by the image sensor subsequent to an emission of electromagnetic radiation with a wavelength from about 513 nm to about 545, a hyperspectral exposure frame generated by the image sensor subsequent to an emission of electromagnetic radiation with a wavelength from about 565 nm to about 585 nm, and/or a hyperspectral exposure frame generated by the image sensor subsequent to an emission of electromagnetic radiation with a wavelength from about 900 nm to about 1000. The hyperspectral exposure frame may include further additional hyperspectral exposure frames that are generated by the image sensor subsequent to other hyperspectral emissions of light as needed based on the imaging application.

A hyperspectral exposure frame may be generated by the image sensor subsequent to an emission of multiple different partitions of electromagnetic radiation. For example, a single hyperspectral exposure frame may be sensed by the pixel array after an emission of electromagnetic radiation with a wavelength from about 513 nm to about 545; from about 565 nm to about 585 nm; and from about 900 nm to about 1000 nm. The emission of electromagnetic radiation may include a single pulse with each of the multiple wavelengths being emitted simultaneously, multiple sub-pulses wherein each sub-pulse is a different wavelength of electromagnetic radiation, or some combination of the above. The emission of electromagnetic radiation with the one or more pulses may occur during a blanking period 316 that occurs prior to the readout period 302 in which the exposure frame is sensed by the pixel array.

In an embodiment, the hyperspectral exposure frame includes a first hyperspectral exposure frame generated by the image sensor subsequent to an emission of electromagnetic radiation with a wavelength from about 565 nm to about 585 nm and a second hyperspectral exposure frame generated by the image sensor subsequent to an emission of electromagnetic radiation with a wavelength from about 900 nm to about 1000 nm. In a further embodiment, the hyperspectral exposure frame includes a first hyperspectral exposure frame generated by the image sensor subsequent to an emission of electromagnetic radiation with a wavelength from about 513 nm to about 545 nm and a second hyperspectral exposure frame generated by the image sensor subsequent to an emission of electromagnetic radiation with a wavelength from about 900 nm to about 1000 nm.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 302. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a hyperspectral 624 emission and sensing reflected electromagnetic energy 626 subsequent to each of the one or more emissions of the hyperspectral 624 emission.

The process illustrated in FIG. 6B provides a higher resolution image and provides a means for generating an RGB image that further includes hyperspectral imaging data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Hyperspectral pulse;
  viii. (Repeat)

As can be seen in the example, a hyperspectral partition may be pulsed at a rate differing from the rates of the other partition pulses. This may be done to emphasize a certain aspect of the scene, with the hyperspectral data simply being overlaid with the other data in the video output to make the desired emphasis. It should be noted that the addition of a hyperspectral partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a hyperspectral partition pulse that is represented less in a pulse pattern results in an increase of less than 20% of the cycling speed of the sensor to accommodate the irregular partition sampling.

In various embodiments, the pulse cycle may include any of the following wavelengths in any suitable order. Such wavelengths may be particularly suited for generating hyperspectral imaging data:
  i. 513 nm to 545 nm;
  ii. 565 nm to 585 nm;
  iii. 1900 nm to 2000 nm;
  iv. 513±5 nm;
  v. 513±10 nm;
  vi. 513±20 nm;
  vii. 513±30 nm;
  viii. 513±35 nm;
  ix. 545±5 nm;
  x. 545±10 nm;
  xi. 545±20 nm;
  xii. 545±30 nm;
  xiii. 545±35 nm;
  xiv. 565±5 nm;
  xv. 565±10 nm;
  xvi. 565±20 nm;
  xvii. 565±30 nm;
  xviii. 565±35 nm;
  xix. 585±5 nm;
  xx. 585±10 nm;
  xxi. 585±20 nm;
  xxii. 585±30 nm;
  xxiii. 585±35 nm;
  xxiv. 900±5 nm;
  xxv. 900±10 nm;
  xxvi. 900±20 nm;
  xxvii. 900±30 nm;
  xxviii. 900±35 nm;
  xxix. 1000±5 nm;
  xxx. 1000±10 nm;
  xxxi. 1000±20 nm;
  xxxii. 1000±30 nm; or
  xxxiii. 1000±35 nm.

In various embodiments, the pulse cycle pattern may include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
  i. 770±20 nm;
  ii. 770±10 nm;
  iii. 770±5 nm;
  iv. 790±20 nm;
  v. 790±10 nm;
  vi. 790±5 nm;
  vii. 795±20 nm;
  viii. 795±10 nm;
  ix. 795±5 nm;
  x. 815±20 nm;
  xi. 815±10 nm;
  xii. 815±5 nm;
  xiii. 770 nm to 790 nm; and/or
  xiv. 795 nm to 815 nm.

Figure 7A:
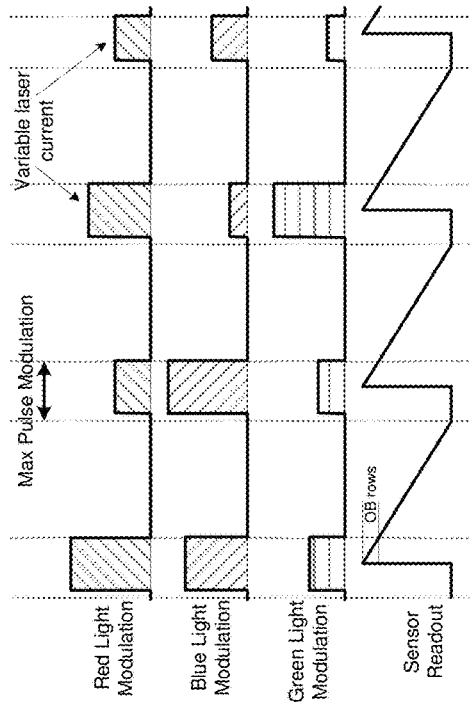
FIGS. 7A-7E illustrate schematic views of processes over an interval of time for recording a frame of video for both full spectrum light and partitioned spectrum light.
Figure 7C:
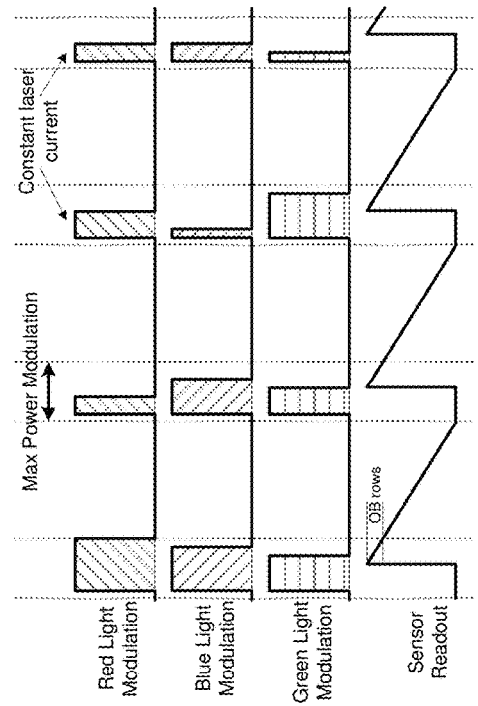
Figure 7B:
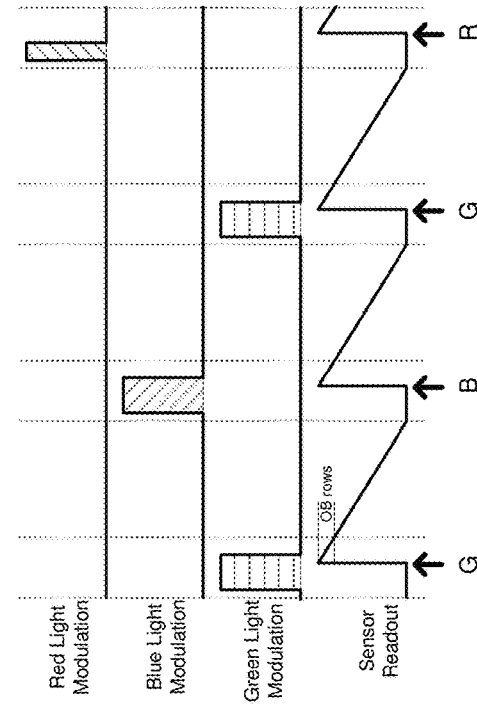

The partition cycles may be divided so as to accommodate or approximate various imaging and video standards. In an embodiment, the partition cycles comprise pulses of electromagnetic energy in the red, green, and blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
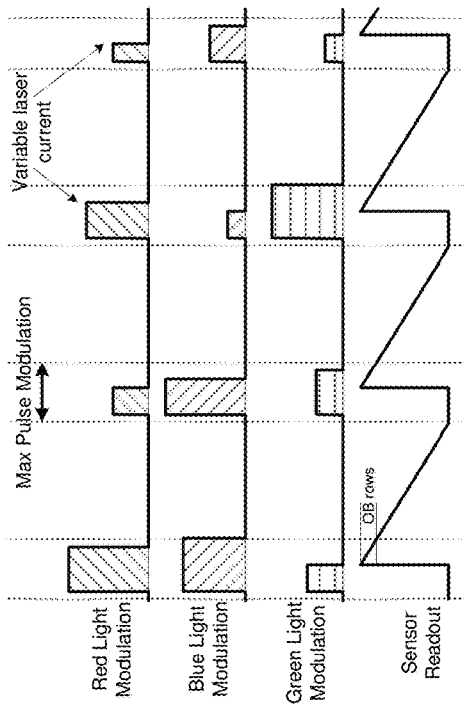

In an embodiment using color spaces green-blue-green-red (as seen in FIG. 7D) it may be desirous to pulse the luminance components more often than the chrominance components because users are generally more sensitive to light magnitude differences than to light color differences. This principle can be exploited using a monochromatic image sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
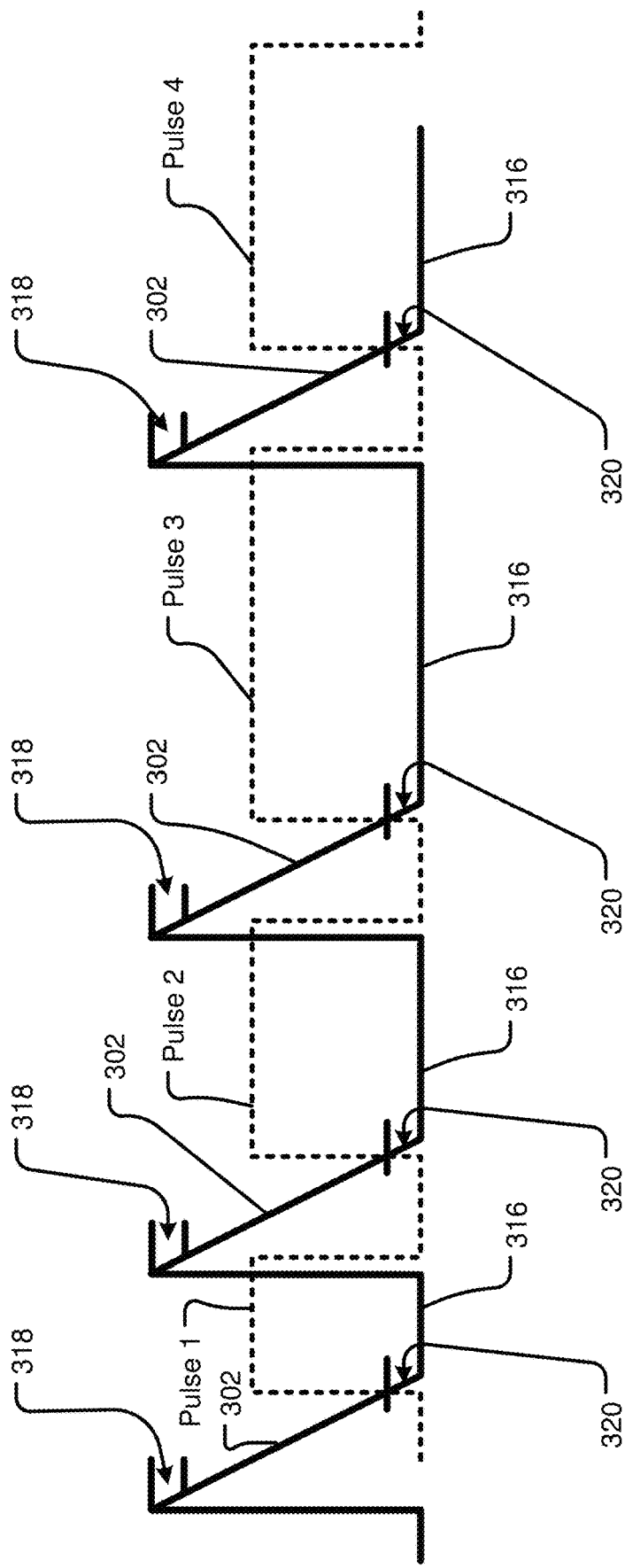

In an embodiment, the pulse of a weaker partition may be duplicated to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking periods with a repeating pattern of two or three or four or n frames.

In FIG. 7E, four different light pulses are illustrated, and Pulse 1 may repeat for example after Pulse 4 and may have a pattern of four frames with different blanking periods. This technique can be used to place the most powerful partition on the smallest blanking period and therefore allow the weakest partition to have wider pulse on one of the next frames without the need of increasing the readout speed. The reconstructed frame can still have a regular pattern from frame to frame as it is constituted of many pulsed frames.

Figure 8:
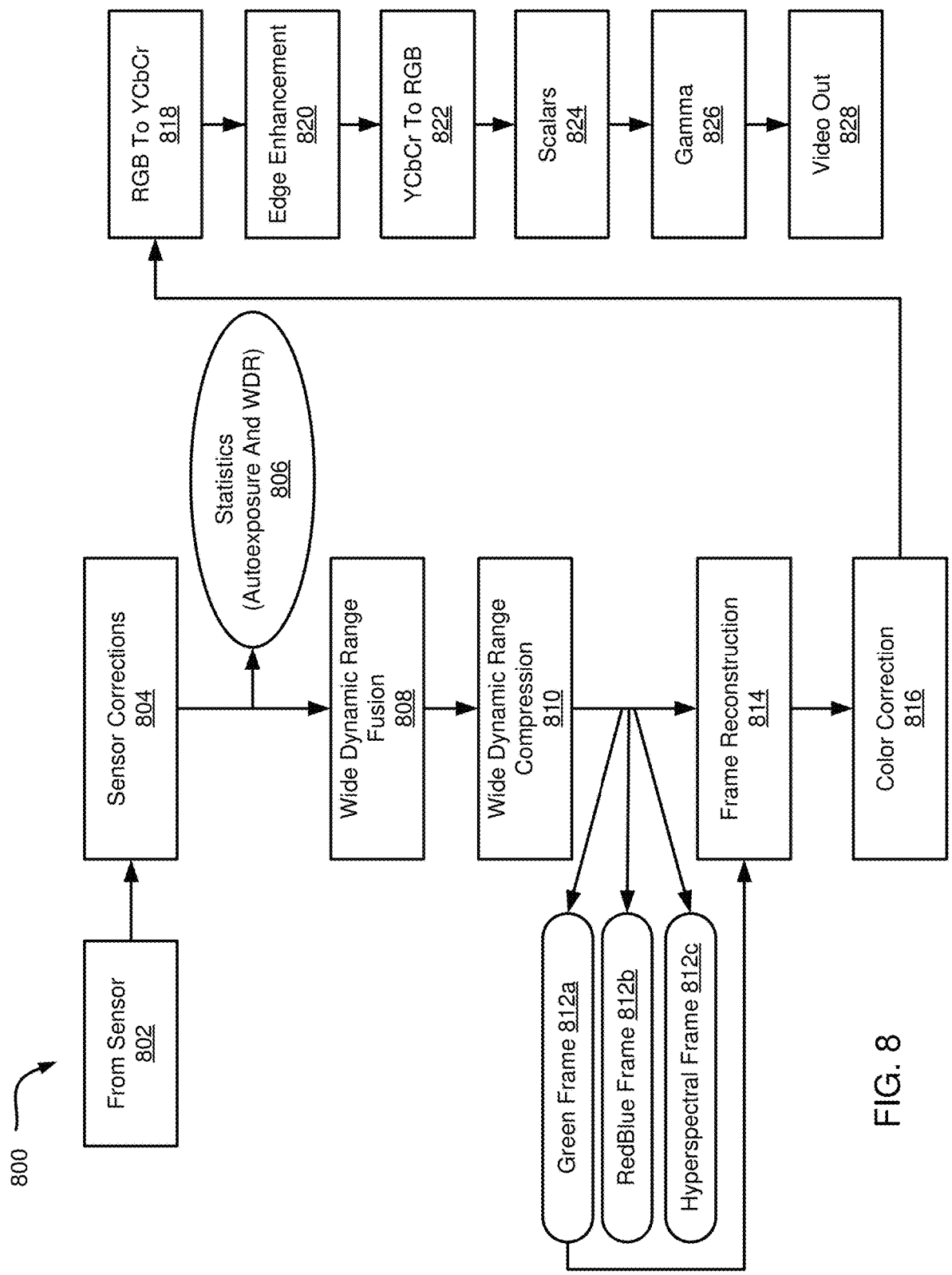
FIG. 8 is a schematic diagram of a process flow to be implemented by a controller or image signal processor for generating a video stream with RGB image frames and hyperspectral data overlaid on the RGB image frame.

FIG. 8 is a schematic diagram of a process flow 800 to be implemented by a controller and/or monochrome image signal processor (ISP) for generating a video stream having RGB images with hyperspectral data overlaid thereon. The process flow 800 results in images having increased dynamic range and spatial resolution. The image signal processor (ISP) chain may be assembled for the purpose of generating RGB image sequences from raw sensor data, yielded in the presence of the G-R-G-B-Hyperspectral light pulsing scheme. In the process flow 800, the first stage is concerned with making corrections to account for any non-idealities in the sensor technology for which it is most appropriate to work in the raw data domain. At the next stage, multiple exposure frames (for example, a green exposure frame 812a, a red-blue exposure frame 812b, and a hyperspectral exposure frame 812c) are buffered because each final exposure frame derives data from multiple raw frames. The frame reconstruction at 814 proceeds by sampling data from a current exposure frame and buffered exposure frames (see 812a, 812b, and/or 812c). The reconstruction process results in full color image frames in linear RGB color space that include hyperspectral image data.

The process flow 800 includes receiving data from an image sensor at 802. Sensor correction calculations are performed at 804. These sensor correction calculations can be used to determine statistics at 806 such as autoexposure settings and wide dynamic range settings. The process flow 800 continues and wide dynamic range fusion is processed at 808. Wide dynamic range compression is processed at 810. The wide dynamic range compression from 810 can be fed to generate the green exposure frame 812a, the red-blue exposure frame 812, and/or the hyperspectral exposure frame 812c. The process flow 800 continues and frame reconstruction is processed at 814 and then color correction is processed at 816. The process flow 800 continues and an RGB (red-green-blue) image is converted to a YCbCr (luminance-chrominance blue-chrominance red) image at 818. Edge enhancement is processed at 820 and then the YCbCr image is converted back to an RGB image at 822. Scalars are processed at 824 and gamma is processed at 826. The video is then exported at 828.

Figure 9:
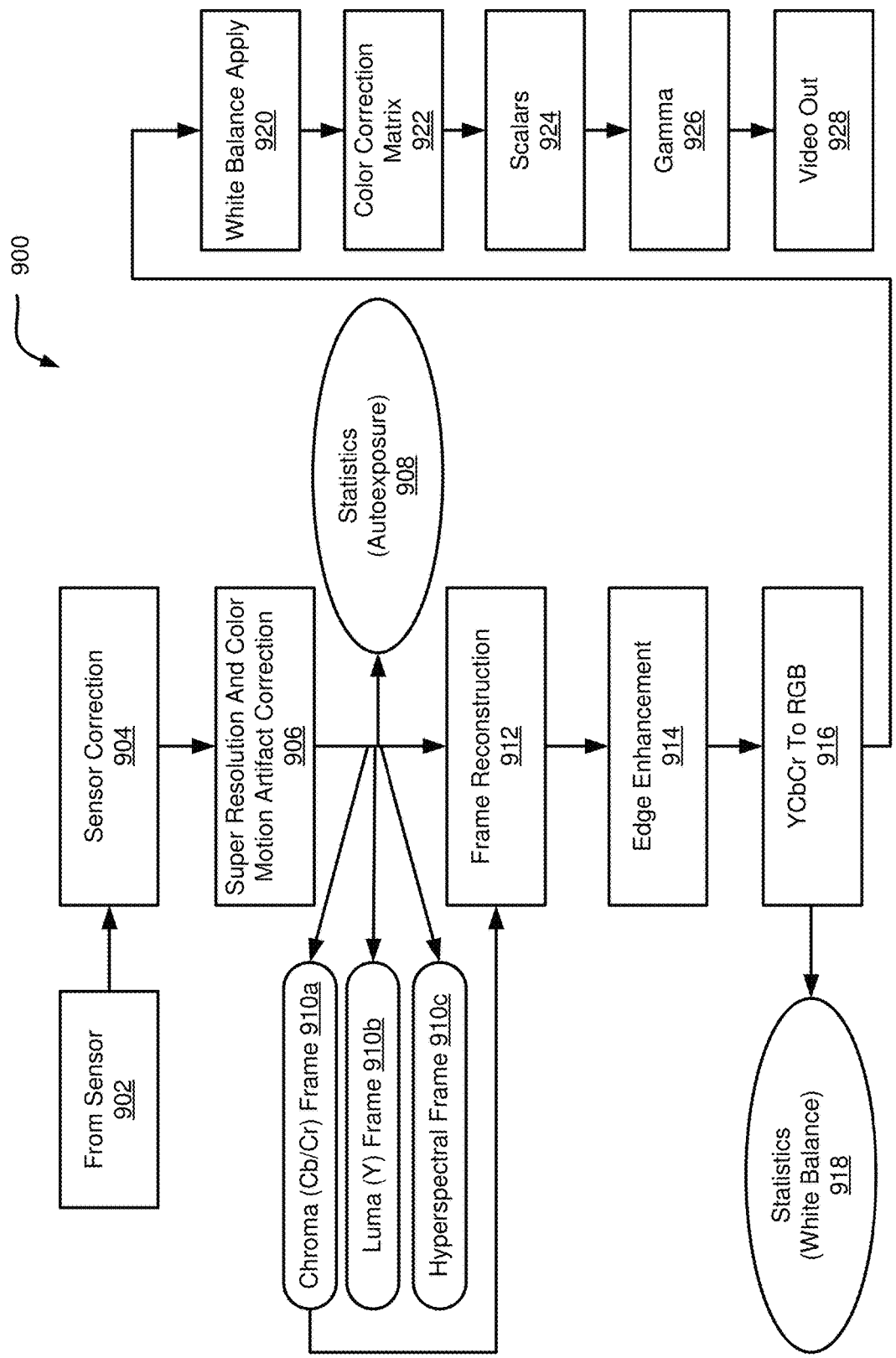
FIG. 9 is a schematic diagram of a process flow for applying super resolution and color motion artifact correction processes to image data that may include luminance, chrominance, and hyperspectral data for generating a YCbCr or RGB image with hyperspectral data overlaid thereon.

FIG. 9 illustrates a process flow 900 for applying the super resolution (SR) and color motion artifact correction (CMAC) processes to image data. The super resolution algorithm uses data from multiple sequential exposure frames that are combined to generate individual image frames with increased spatial resolution. The generation of the individual image frames depends upon accurate motion detection within local regions of the multiple exposure frames. In some implementations, the luminance plane is the most critical plane for determining spatial resolution. If the luminance plane is the most critical plane, then only the adjacent luminance exposure frames are combined in an embodiment. In the case of red-green-blue pulsing according to an R-G-B-G pulsing schedule, only adjacent green exposure frames are combined to generate the individual image frames having higher spatial resolution.

With respect to the discussions regarding FIG. 9, the super resolution algorithm is applied in the context of Y-Cb-Cr light pulsing. YCbCr is a family of color spaces that can be used as part of the color image pipeline in video and digital photography systems. Y' is the luminance component (may be referred to as the "luma" component) and represents the "black-and-white" or achromatic portion of the image. Cb is the blue-difference chrominance component (may be referred to as the "chroma" component) and Cr is the red-difference chrominance component. The chrominance components represent the color information in the image or video stream. Analog RGB image information can be converted into luminance and chrominance digital image information because human vision has finer spatial sensitivity to luminance (black-and-white) differences than chromatic (color) differences. Video and imaging systems can therefore store and transmit chromatic information at lower resolution and optimize perceived detail at a particular bandwidth. Y' (with the prime notation) is distinguished from Y (without the prime notation), where Y is luminance and refers to light intensity. Y'CbCr color spaces are defined by a mathematical coordinate transformation from an associated RGB color space. If the underlying RGB color space is absolute, the Y'CbCr color space is an absolute color space as well.

The use of the super resolution algorithm as disclosed herein is not limited to any particular pulsing scheme and can be applied to YCbCr pulsing or to RGB pulsing. The super resolution algorithm may further be applied to hyperspectral and/or fluorescence image data. In an embodiment, the endoscopic imaging system disclosed herein pulses light to generate at least four types of captured frames. The captured exposure frames include a Y exposure frame that contains pure luminance information, a Cb exposure frame which contains a linear sum of Y and Cb data, and a Cr exposure frame which contains a linear sum of Y and Cr data. During frame reconstruction (i.e. color fusion). There may be one full color image frame in the YCbCr color space that is generated for each luminance exposure frame at the input. The luminance data may be combined with the chrominance data from the frame prior to and the frame following the luminance frame. Note that given this pulsing sequence, the position of the Cb frame with respect to the Y frame ping-pongs between the before and after slots for alternate Y cases, as does its complementary Cr component. Therefore, the data from each captured Cb or Cr chrominance frame may be utilized in two resultant full-color image frames. The minimum frame latency may be provided by performing the color fusion process during chrominance (Cb or Cr) frame capture.

The super resolution algorithm (see 906) enhances the resolution of an image frame by combining multiple exposure frames. Data from multiple sequential exposure frames is combined to increase the spatial resolution of the resultant image frame. The super resolution algorithm depends on accurate motion detection within local regions of the scene across the multiple exposure frames. The super resolution algorithm combines non-redundant information from the multiple exposure frames to generate a high-resolution image frame. The non-redundant information in the multiple exposure frames can be introduced by subpixel shifts between the multiple exposure frames. The subpixel shifts may occur due to uncontrolled motions by objects within the scene or by the imaging system itself. In an embodiment, the super resolution algorithm includes aligning the multiple exposure frames to pixel-level or subpixel-level accuracy and combining the multiple exposure frames into a high resolution image grid. There are numerous methods of applying a super resolution algorithm and any suitable method may be applied for combining the multiple exposure frames.

In an embodiment, the super resolution algorithm relies on the luminance plane to accurately detect motion within local regions of a scene captured by the multiple exposure frames. The luminance plane is the most critical for spatial resolution, and so the super resolution algorithm can be applied to luminance exposure frames in the case of Y-Cb-Cr light pulsing. In the case of R-G-B-G light pulsing, the super resolution algorithm can be applied to the green exposure frames. Embodiments of the disclosure are described in the context of the Y-Cb-Cr light pulsing scheme. However, it should be appreciated that the methods and systems described herein are not restricted to the Y-Cb-Cr pulsing scheme and can be applied to the R-G-B-G pulsing scheme. When the methods and systems are applied to the R-G-B-G pulsing scheme, the green exposure frame takes the place of the luminance exposure frame, the red exposure frame takes the place of the Cr exposure frame, and the blue exposure frame takes the place of the Cb exposure frame.

Referring again to the process flow 900 illustrated in FIG. 9, data from a sensor is input at 902. Sensor correction 904 is performed on the sensor data. The super resolution (SR) and color motion artifact correction (CMAC) algorithms are implemented at 906. The SR and CMAC processes 906 may be performed within the camera image signal processor on raw, captured sensor data. The SR and CMAC processes can be performed at 906 immediately after all digital sensor correction 904 processes are completed. The SR and CMAC processes 906 can be executed before the sensor data is fused into linear RGB or YCbCr space color images. Statistics can be exported at 908 to determine the appropriate autoexposure for the image.

A chrominance exposure frame 910a and a luminance exposure frame 910b are constructed. In an embodiment, a hyperspectral exposure frame 910c is also constructed. The luminance exposure frame 910b is constructed based on the Y frames in arrival order. The chrominance exposure frames 910a are constructed based on the Cb and Cr frames in arrival order. The number of frames processed by the super resolution algorithm is an optional variable. The first-in-first-out depth of the luminance exposure frame 910b is normally odd and its size can be determined based on available processing, memory, memory-bandwidth, motion detection precision, or acceptable latency considerations. The color motion artifact correction process can be performed with the minimum first-in-first-out depth of three frames for Y and two frames for Cb and/or Cr. The super resolution algorithm may generate better resolution by the use of five luminance frames.

The super resolution process itself may involve combining data from multiple luminance exposure frames into a central super-resolved frame, which is stationary with respect to the luminance first-in-first-out (may be referred to as the RY buffer). For each of the non-central luminance buffers, an upscaled version is produced in which individual blocks are shifted according to their (x,y) motion vectors. Any pixels at the upscaled resolution that are not filled after shifting are left blank.

The image data is processed to implement frame reconstruction at 912 and edge enhancement at 914. The YCbCr image is converted to an RGB image at 916. Statistics on the RGB image can be exported at 918 to determine appropriate white balance. The appropriate white balance is applied at 920 and entered into the color correction matric at 922. Scalars 924 and gamma 926 are determined and the video is exported out at 928. The process flow 900 can be implemented in the camera image signal processor in real-time while image data is captured and received from the sensor (see 902).

During frame reconstruction 912, there may be one full color image frame in YCbCr space generated for each luminance exposure frame. The data captured in the luminance exposure frame may be combined with data from chrominance exposure frames captured before and after the luminance exposure frame. Given this pulsing sequence, the position of the Cb exposure frame with respect to the luminance exposure frame may be adjusted to occur before or after the luminance exposure frame for alternate luminance cases. The same is true for the Cr exposure frame with respect to the luminance exposure frame. Therefore, the data from each captured Cb or Cr exposure frame is used in two resultant full color images. The minimum frame latency may be provided by performing the frame reconstruction 912 process during the Cb and Cr frame capture.

In an embodiment, two frame first-in-first-out (FIFO) flows are constructed. One FIFO is constructed for luminance exposure frames in arrival order and another FIFO is constructed for Cb exposure frames and Cr exposure frames. The number of frames to use for the super resolution (see 906) process is an optional variable. The luminance FIFO depth may be odd, and its size may be determined by the available processing, memory, or memory bandwidth, or by motion detection precision or acceptable latency considerations. The color motion artifact correction (CMAC) at 906 may be performed with the minimum FIFO depth of three luminance exposure frames and two chrominance exposure frames. For the super resolution algorithm, the use of five luminance exposure frames results in improved resolution. On luminance exposure frames, the current object frame is the central in the luminance FIFO. On chrominance exposure frames the two chrominance exposure frames that flank the central luminance exposure frame are adjusted to line up motion to the central luminance exposure frame.

Figure 10:
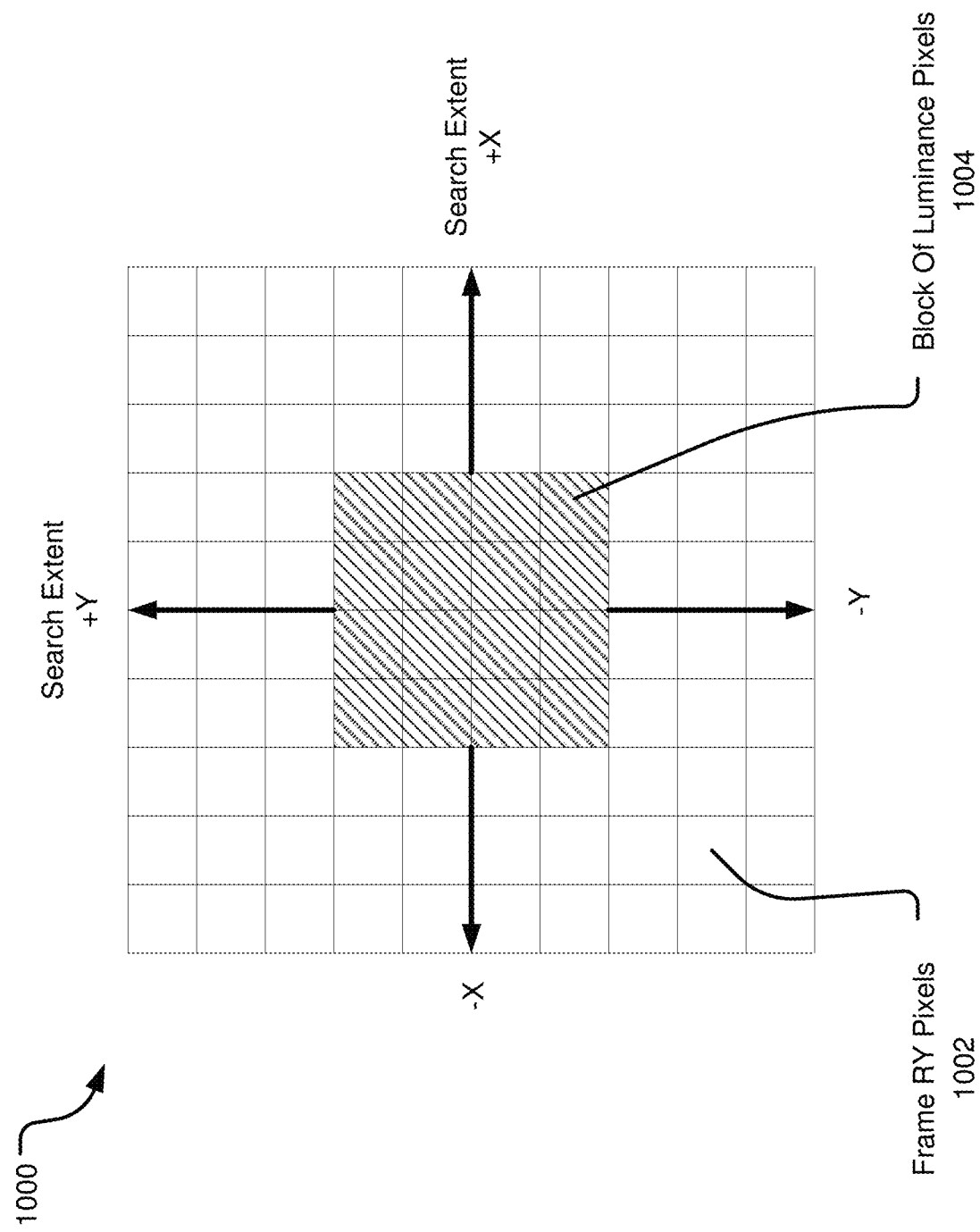
FIG. 10 is a schematic of an example pixel array configured in an x and y plane that may be used to implement the process flow illustrated in FIG. 9 for applying the super resolution and color motion artifact correction processes to image data.

FIG. 10 is a schematic of an example pixel array 1000 that may be used to implement the process flow 900 illustrated in FIG. 9. The pixel array 1000 includes a block of luminance pixels 1004 for generating data for a Y luminance exposure frame. The pixel array 1000 includes RY pixels 1002 framing the block of luminance pixels 1004. The RY pixels 1002 are buffered first-in-first-out pixels.

On a luminance exposure frame, the current object frame is the central block of luminance pixels 1004 in the first-in-first-out. On chrominance frames, the Cb and Cr frames flank the central block of luminance pixels 1004. This is adjusted to line up motion to the central block of luminance pixels 1004 to detect motion.

The super resolution and CMAC algorithms (see 906) rely on motion detection. In an embodiment, a motion detection method includes block matching which provides x and y motion vectors for small, independent blocks of pixels of configurable dimensions. There are other motion detection algorithms that may be used in other implementations. Bock matching offers advantages for simplicity of implementation and particularly for real time processing in hardware. In an embodiment, a two-stage match process is described which provides for a super resolved frame with two times the pixel count in the x and y directions. Further stages may be added to increase the pixel count further. However, many more buffered frames and computations would be required to make this worthwhile. In an embodiment, in addition to the raw, buffered, luminance exposure frames disposed in the middle of the luminance FIFO (referred to as frame RY pixels) 1002, three two-times upscaled versions of the middle block of luminance pixels 1004 are created. The middle block of luminance pixels 1004 may be upscaled using bilinear interpolation (referred to as buffer BL). In an additional exposure frame, the block of luminance pixels 1004 may be upscaled using bicubic interpolation (referred to as buffer BC). In an additional exposure frame, the block of luminance pixels 1004 may be upscaled with no interpolation such that the upscaled frame includes only zeros in the place of empty pixels (referred to as NI). The bilinear interpolation may be used in the block matching method. The no interpolation forms the baseline for the super resolved frame. The bicubic interpolation may serve as a fallback pixel source for unfilled pixels within the super resolved frame.

Figure 11:
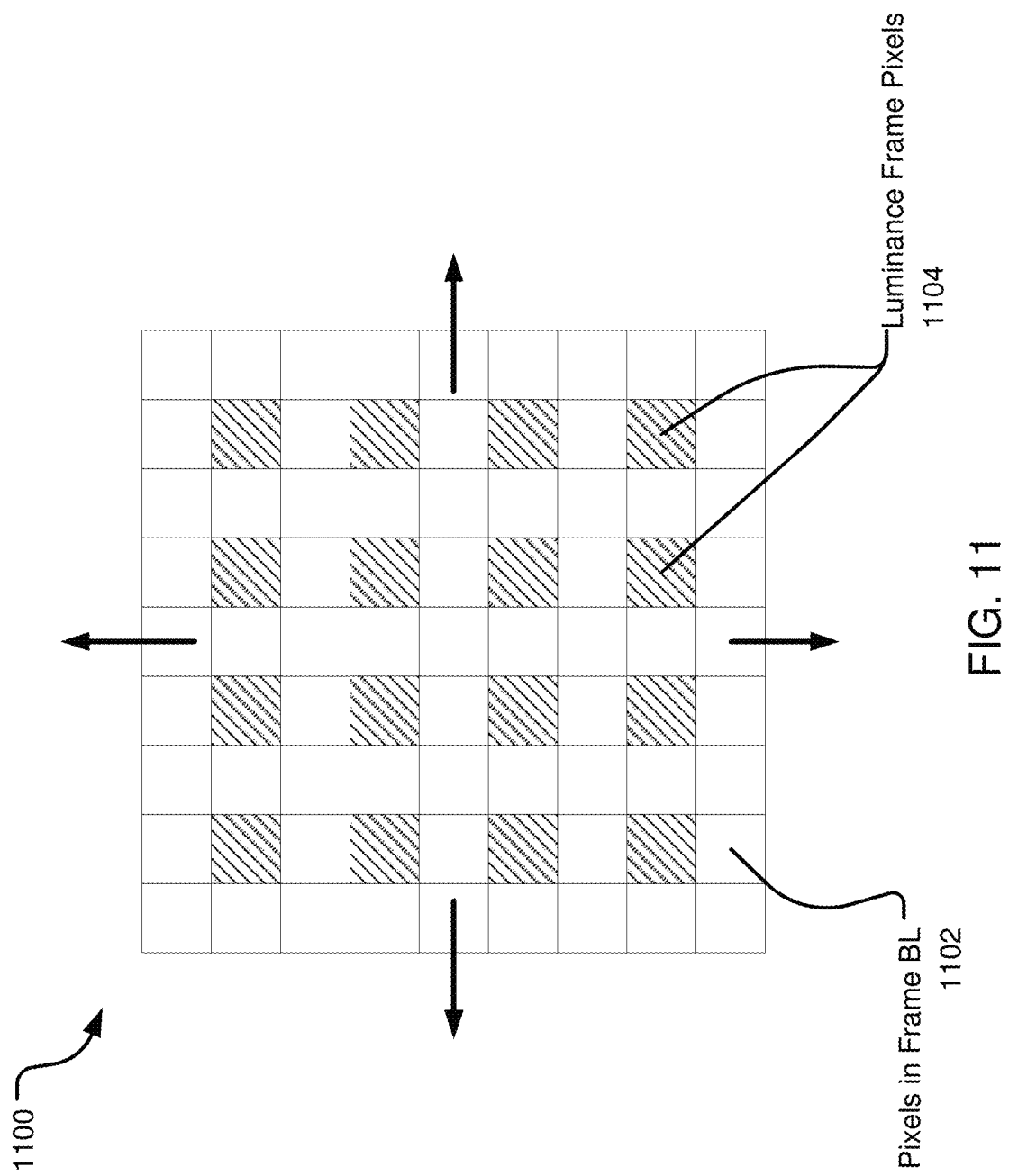
FIG. 11 is a schematic of an example pixel array wherein luminance pixels are shifted in the x and y directions for comparing pixel data to an equivalent block in that location in a different exposure frame in furtherance of applying super resolution and color motion artifact processes to image data.

FIG. 11 illustrates a schematic of a pixel array 1100 with luminance frame pixels 1104 disbursed within pixels frame BL 1102. For each luminance exposure frame in the buffer, except for the frame RY pixels 1002, the pixel array may be segmented into square blocks of some dimension as illustrated in FIG. 10. Each block is shifted around, one pixel at a time, in both x and y directions, within some defined range of shifts in both positive and negative directions. For each pixel location, the pixel data may be compared to the equivalent block sitting in that location with the object frame RY pixels 1002. The x and y shifts encountered for the best match position become the recorded Cartesian motion coordinates for all pixels within the block. This process is depicted in FIG. 11.

In the pixel array 1100, for each luminance exposure frame in the buffer, except for RY, the pixel array 1000 shown in FIG. 10 may be segmented into square blocks of some dimension, (e.g. 4×4). Each block is shifted around, one pixel at a time, in both x and y, within some defined range of shifts in both positive and negative directions (e.g. +/−3 pixels). For each location within the pixel array, a pixel may be compared to an equivalent block sitting in that location with the object frame, RY. The x and y shifts encountered for the best match position become the recorded Cartesian motion coordinates for all pixels within the pixel array 1100. There are various ways to make the comparison and a relatively convenient metric is the modulus of the pixel differences, (i.e. between the stationary pixel in RY and the corresponding pixel in the block under study), summed over all pixels in the pixel array 1100. The best match may be taken as the minimum of this value. It can also be recorded for each block as a matching quality metric, which may be used to arbitrate between competing pixels during the spatial resolution process.

There are various ways to make this comparison. In an embodiment, a metric is calculated based on the modulus of the pixel differences, i.e., between the stationary pixel in the frame RY pixels 1002 and the corresponding pixels in the block under study, summed over all pixels in the block. The best match may be taken as the minimum of this value. The best match can be recorded for each block as a matching quality metric that may be used to arbitrate between competing pixels during the super resolution algorithm (see 906). Alternatively, the minimum sum of squared differences may be used as the matching matric. At this stage, each pixel within non-RY luminance frames has a motion estimate that is quantized at the captured resolution. In an implementation where 2X resolution is sought, the method includes comparing a block of pixels within the non-RY frames to the BL buffer. This begins from the best shifted position according to the recorded motion vectors. Shifts are performed by shifting one-half pixel in the positive and negative directions to give a total of nine possible positions. A half pixel in the luminance frame under study is one whole pixel with respect to BL. Of those nine possible pixel positions, the best match is again determined, and the recorded motion vector is adjusted accordingly. If the motion vector at this stage has a half integer component, then the motion vector has the potential to enhance the resolution of the resultant image frame.

Motion vectors for the two luminance exposure frames flanking RY may be saved for the CMAC process. The CMAC process may be performed during the chrominance exposure frames. The super resolution process itself may include combining data from multiple exposure frames in a central super resolved frame. The central super resolved frame is stationary with respect to the RY buffer. For each of the non-central luminance buffers a 2× upscaled version is generated in which the individual blocks have been shifted according to their (x,y) motion vectors. Any pixels at the 2× resolution that are not filled after shifting are left blank.

The basis of the super resolved frame is the NI buffer which is the upscaled version of RY with no interpolation. Three of every four pixels in NI may be initially blank. The primary objective may be to fill the pixels with data from the upscaled and shifted luminance buffers. One approach is to scan the pixels for the first match for each empty pixel. At the end, any pixels still blank may be filled in from the BC buffer. Another approach is to assess possible candidates and select the best candidate based on a parameter that has been logged as a motion estimate quality metric. An example of a motion estimate quality metric is the minimum sum of absolute differences for the originating block or some derivative thereof. Another approach is to combine all candidates in some way, e.g., average the candidates or perform a weighted average according to a quality parameter. In such an approach, even non-zero pixels in NI can be substituted. The benefit of such an approach is that in addition to enhancing the resolution, the net signal to noise ratio is also improved. Candidates with notably poor quality values can also be rejected.

Each pixel within non-RY, luminance frames, has a motion estimate that is quantized at the captured resolution. If X2 super resolution is sought, the next stage involves, for block of pixels within the non-RY frames, comparing to the BL buffer instead of the RY buffer. Starting from the best shifted position (according to the recorded motion vectors). Shifts can be performed by positive and negative half-pixel, giving a total of nine possible positions as shown in FIG. 11. Of those nine possible pixel positions, the best match is again determined, and the recorded motion vector is adjusted accordingly.

Motion vectors for the luminance frames flanking RY frames may be saved for the color motion artifact correction (CMAC) process which occurs during the C frames. The basis of the super-resolved frame is the NI buffer which is the upscaled version of RY with no interpolation. Three out of every four pixels in NI may be initially blank, and the primary objective is to fill them with data from the upscaled & shifted luminance buffers. At the end, any pixels which are still blank may be filled in from the BC buffer which is the bicubic interpolated version of the central luminance frame. A more sophisticated approach to filling may be to assess all possible candidates and choose the best one based on some parameter that has been logged as a motion estimate quality metric. An example of such a metric could be the minimum sum of absolute differences for the originating block, or some derivative thereof. This requires at least one additional frame buffer per luminance frame. Alternatively, all candidates can be combined in some way, e.g. as an average which can be weighted according to a quality parameter. Candidates with notably poor quality values can also be rejected altogether.

Figure 12:
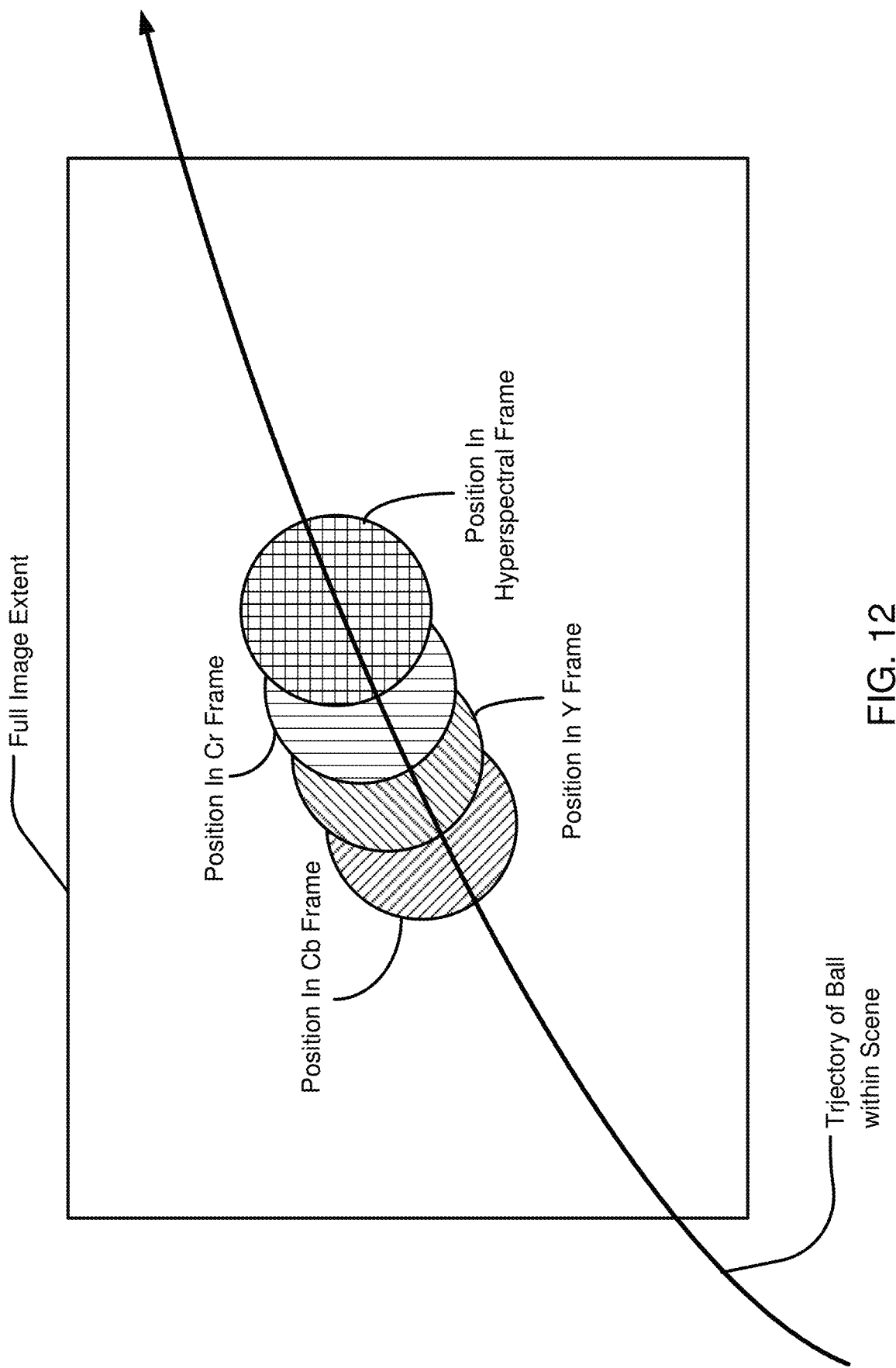
FIG. 12 illustrates an example scene wherein a ball is traveling through the scene at a quicker rater than the rate of capture for multiple exposure frames sensed by a pixel array of an image sensor.

FIG. 12 illustrates the issue of significant motion from frame to frame with framewise color modulation. FIG. 12 illustrates an example in which a ball is traveling through the scene at a quicker rate than the rate of capture for the Cb exposure frame, the Y exposure frame, the Cr exposure frame, and the hyperspectral exposure frame. The ball is moving on a trajectory across the scene during capture that results in different positions for the Y, Cb, Cr, and hyperspectral exposure frames. The basis of the color motion artifact correction is to utilize the relative motion estimation for adjacent luminance (Y) frames to predict the motion that occurred for the intermediate Cb, Cr, and hyperspectral exposure frames relative to the luminance frame.

In an embodiment, the motion vectors for adjacent luminance frames are assessed and divided by two. This assumes that any motion that has occurred from luminance frame to luminance frame is linear. If motion estimation is available for three or more luminance frames in addition to the object frame (RY), then bicubic interpolation may be employed for a more precise interpolation. The pixel shifting can take place either at the original or the doubled resolution following a bicubic upscale. Either way, after shifting, there are many void locations with various random shapes and sizes which may be filled in to ensure good image quality.

The application of motion information can be different for color motion artifact correction (CMAC) compared with super resolution. Super resolution uses a bicubic upscaled version of RY as a default, so the worst case is that a pixel void is filled by interpolation using the sixteen closest neighbors in the correct motion frame. For CMAC, there may be no predicting the distance of the nearest filled neighbors such that the known information is limited to the original block search distance divided by two. Some means of interpolation are required to fill in the holes. One way to do this is for each missing pixel, find the distance to the closest filled pixel in the positive and negative x and y directions, and then fill with an average level that has been weighted according to the reciprocal of each distance.

Figure 13:
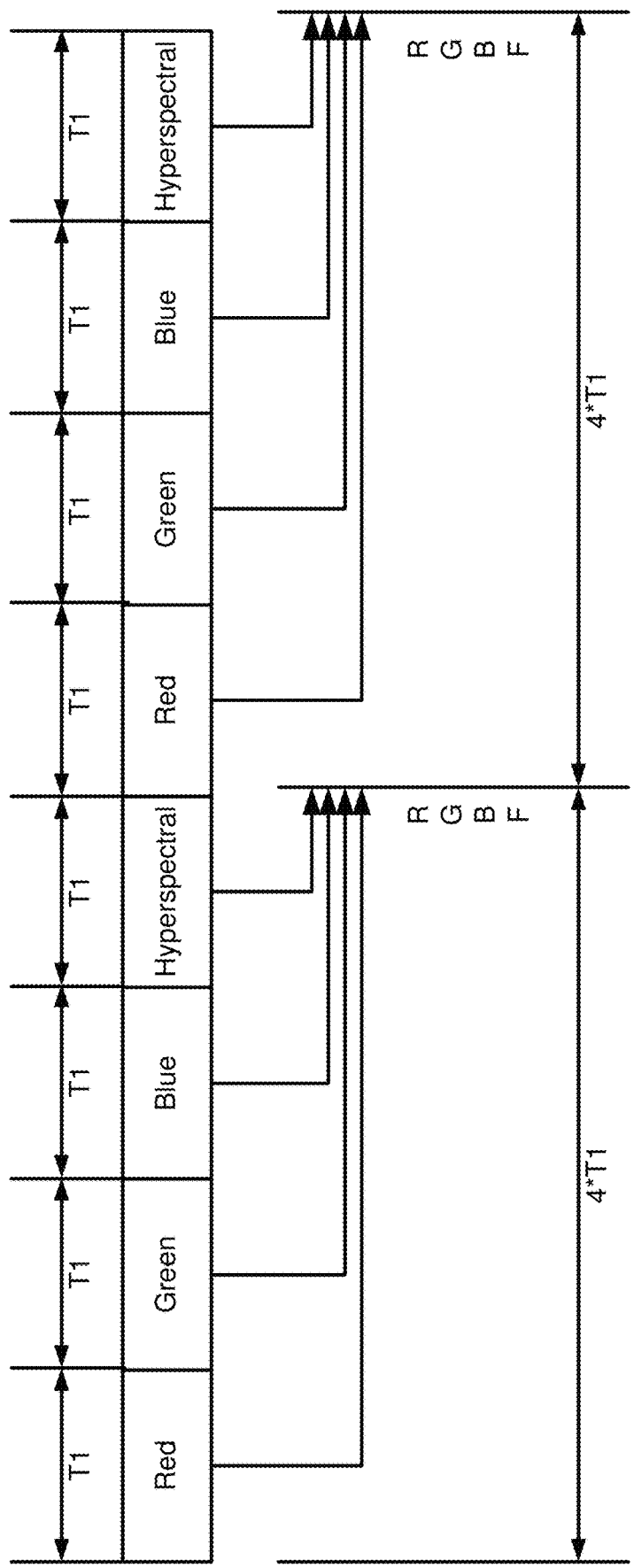
FIG. 13 is a schematic diagram of a pattern reconstruction process for generating an RGB image frame with hyperspectral image data overlaid thereon.

FIG. 13 is a schematic diagram of a pattern reconstruction process. The example pattern illustrated in FIG. 13 includes Red, Green, Blue, and Hyperspectral pulses of light that each last a duration of T1. It should be appreciated that the pattern reconstruction process illustrated in FIG. 13 can also be applied to a Y-Cb-Cr-Hyperspectral pulsing scheme. In various embodiments, the pulses of light may be of the same duration or of differing durations. The Red, Green, Blue, and Hyperspectral exposure frames are combined to generate an RGB image with hyperspectral data overlaid thereon. A single image frame comprising a red exposure frame, a green exposure frame, a blue exposure frame, and a hyperspectral exposure frame requires a time period of 4*T1 to be generated. The time durations shown in FIG. 13 are illustrative only and may vary for different implementations. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

In an embodiment, the dynamic range of the system is increased by varying the pixel sensitivities of pixels within the pixel array of the image sensor. Some pixels may sense reflected electromagnetic radiation at a first sensitivity level, other pixels may sense reflected electromagnetic radiation at a second sensitivity level, and so forth. The different pixel sensitivities may be combined to increase the dynamic range provided by the pixel configuration of the image sensor. In an embodiment, adjacent pixels are set at different sensitivities such that each cycle includes data produced by pixels that are more and less sensitive with respect to each other. The dynamic range is increased when a plurality of sensitivities are recorded in a single cycle of the pixel array. In an embodiment, wide dynamic range can be achieved by having multiple global TX, each TX firing only on a different set of pixels. For example, in global mode, a global TX1 signal is firing a set 1 of pixels, a global TX2 signal is firing a set 2 of pixel, a global TXn signal is firing a set n of pixels, and so forth.

Figure 14A:
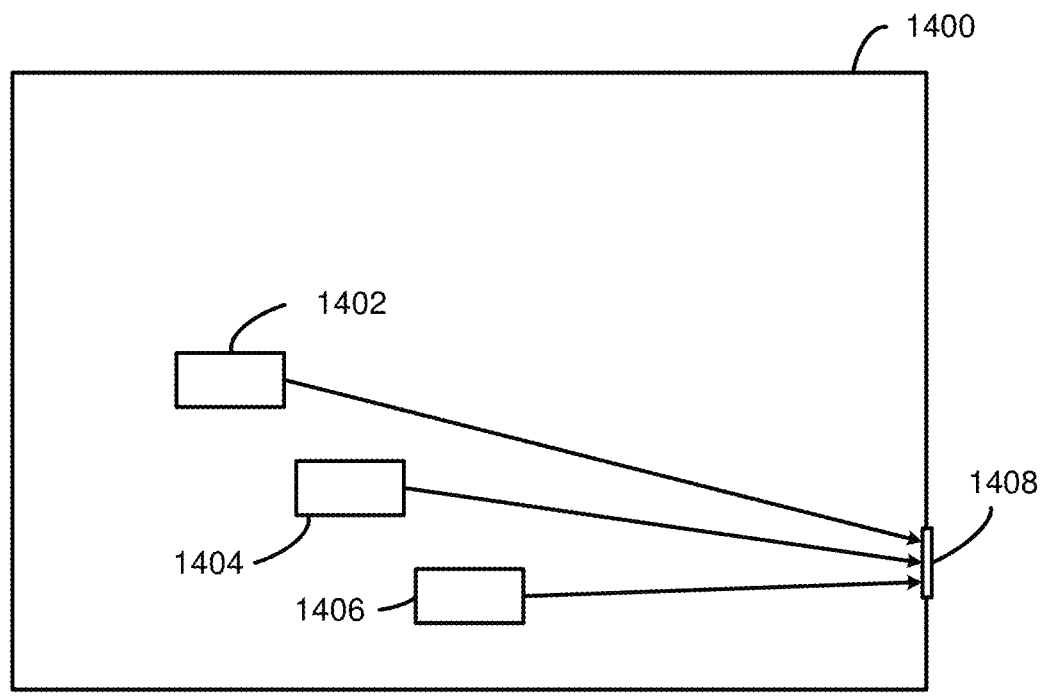
FIGS. 14A-14C illustrate a light source having a plurality of emitters.
Figure 14B:
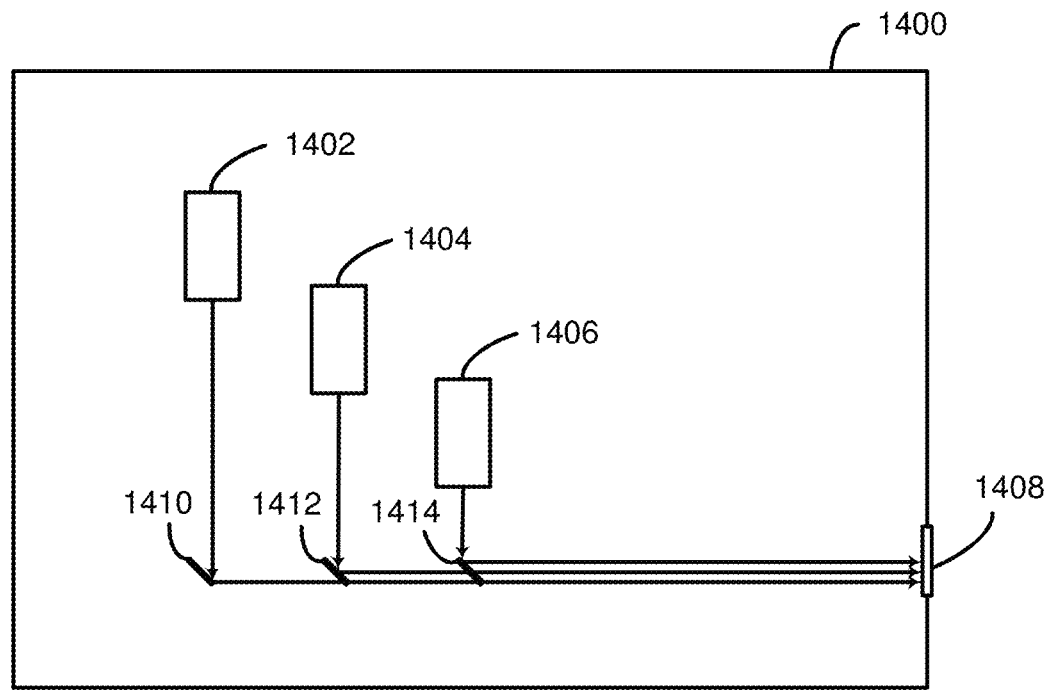
Figure 14C:
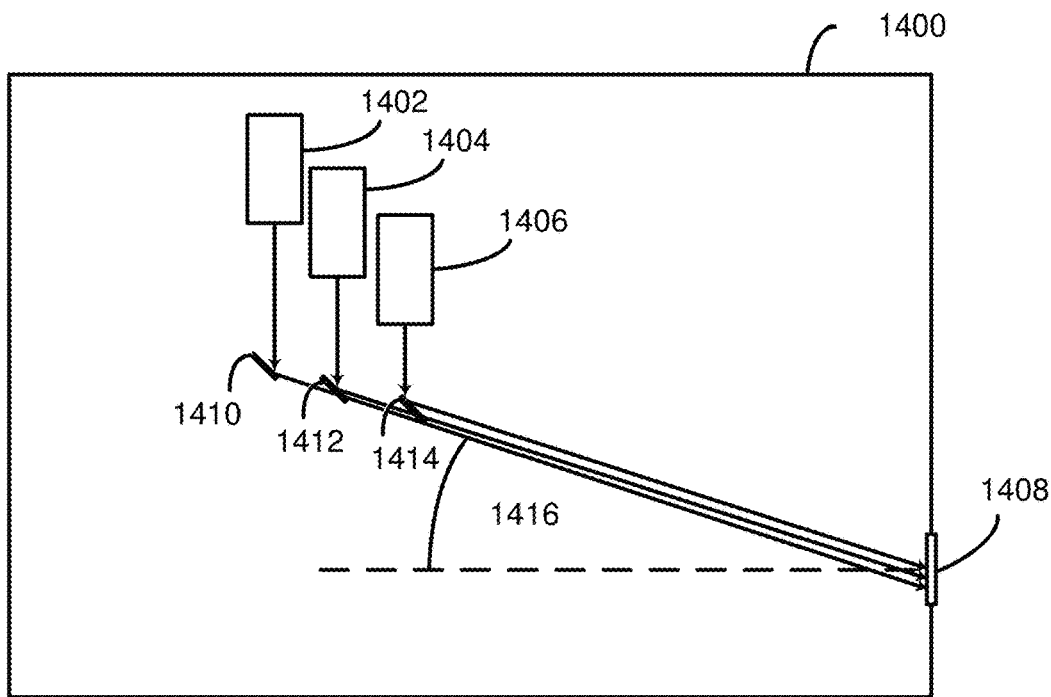

FIGS. 14A-14C each illustrate a light source 1400 having a plurality of emitters. The emitters include a first emitter 1402, a second emitter 1404, and a third emitter 1406. Additional emitters may be included, as discussed further below. The emitters 1402, 1404, and 1406 may include one or more laser emitters that emit light having different wavelengths. For example, the first emitter 1402 may emit a wavelength that is consistent with a blue laser, the second emitter 1404 may emit a wavelength that is consistent with a green laser, and the third emitter 1406 may emit a wavelength that is consistent with a red laser. For example, the first emitter 1402 may include one or more blue lasers, the second emitter 1404 may include one or more green lasers, and the third emitter 1406 may include one or more red lasers. The emitters 1402, 1404, 1406 emit laser beams toward a collection region 1408, which may be the location of a waveguide, lens, or other optical component for collecting and/or providing light to a waveguide, such as the jumper waveguide 206 or lumen waveguide 210 of FIG. 2.

In an implementation, the emitters 1402, 1404, and 1406 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 1402, 1404, and 1406 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 1402, 1404, and 1406 emit a laser scanning pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 1402, 1404, and 1406 may emit a laser scanning pattern such that a laser scanning pattern is projected on to each tool individually. In such an embodiment, the laser scanning data for each of the tools can be analyzed to identify distances between the tools and other objects in the scene.

In the embodiment of FIG. 14B, the emitters 1402, 1404, 1406 each deliver laser light to the collection region 1408 at different angles. The variation in angle can lead to variations where electromagnetic energy is located in an output waveguide. For example, if the light passes immediately into a fiber bundle (glass or plastic) at the collection region 1408, the varying angles may cause different amounts of light to enter different fibers. For example, the angle may result in intensity variations across the collection region 1408. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 1402, 1404, 1406 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 1408 is represented as a physical component in FIG. 14A, the collection region 1408 may simply be a region where light from the emitters 1402, 1404, and 1406 is delivered. In some cases, the collection region 1408 may include an optical component such as a diffuser, mixing rod, lens, or any other intervening optical component between the emitters 1402, 1404, 1406 and an output waveguide.

FIG. 14C illustrates an embodiment of a light source 1400 with emitters 1402, 1404, 1406 that provide light to the collection region 1408 at the same or substantially same angle. The light is provided at an angle substantially perpendicular to the collection region 1408. The light source 1400 includes a plurality of dichroic mirrors including a first dichroic mirror 1410, a second dichroic mirror 1412, and a third dichroic mirror 1414. The dichroic mirrors 1410, 1412, 1414 include mirrors that reflect a first wavelength of light but transmit (or are transparent to) a second wavelength of light. For example, the third dichroic mirror 1414 may reflect blue laser light provided by the third emitter, while being transparent to the red and green light provided by the first emitter 1402 and the second emitter 1404, respectively. The second dichroic mirror 1412 may be transparent to red light from the first emitter 1402, but reflective to green light from the second emitter 1404. If other colors or wavelengths are included dichroic mirrors may be selected to reflect light corresponding to at least one emitter and be transparent to other emitters. For example, the third dichroic mirror 1414 reflect the light form the third emitter 1406 but is to emitters "behind" it, such as the first emitter 1402 and the second emitter 1404. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 1408 at a substantially same angle.

Because the dichroic mirrors allow other wavelengths to transmit or pass through, each of the wavelengths may arrive at the collection region 1408 from a same angle and/or with the same center or focal point. Providing light from the same angle and/or same focal/center point can significantly improve reception and color mixing at the collection region 1408. For example, a specific fiber may receive the different colors in the same proportions they were transmitted/reflected by the emitters 1402, 1404, 1406 and mirrors 1410, 1412, 1414. Light mixing may be significantly improved at the collection region compared to the embodiment of FIG. 14B. In one embodiment, any optical components discussed herein may be used at the collection region 1408 to collect light prior to providing it to a fiber or fiber bundle.

FIG. 14C illustrates an embodiment of a light source 1400 with emitters 1402, 1404, 1406 that also provide light to the collection region 1408 at the same or substantially same angle. However, the light incident on the collection region 1408 is offset from being perpendicular. Angle 1416 indicates the angle offset from perpendicular. In one embodiment, the laser emitters 1402, 1404, 1406 may have cross sectional intensity profiles that are Gaussian. As discussed previously, improved distribution of light energy between fibers may be accomplished by creating a more flat or top-hat shaped intensity profile. In one embodiment, as the angle 1416 is increased, the intensity across the collection region 1408 approaches a top hat profile. For example, a top-hat profile may be approximated even with a non-flat output beam by increasing the angle 1416 until the profile is sufficiently flat. The top hat profile may also be accomplished using one or more lenses, diffusers, mixing rods, or any other intervening optical component between the emitters 1402, 1404, 1406 and an output waveguide, fiber, or fiber optic bundle.

Figure 15:
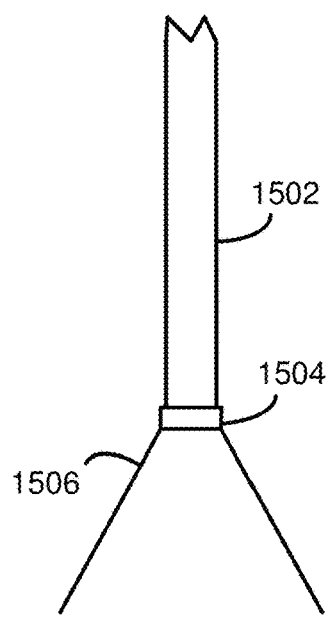
FIG. 15 illustrates a single optical fiber outputting via a diffuser at an output to illuminate a scene in a light deficient environment.

FIG. 15 is a schematic diagram illustrating a single optical fiber 1502 outputting via a diffuser 1504 at an output. In one embodiment, the optical fiber 1502 has a diameter of 500 microns, a numerical aperture of 0.65, and emits a light cone 1506 of about 70 or 80 degrees without a diffuser 1504. With the diffuser 1504, the light cone 1506 may have an angle of about 110 or 120 degrees. The light cone 1506 may be a majority of where all light goes and is evenly distributed. The diffuser 1504 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 14A-14C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 16:
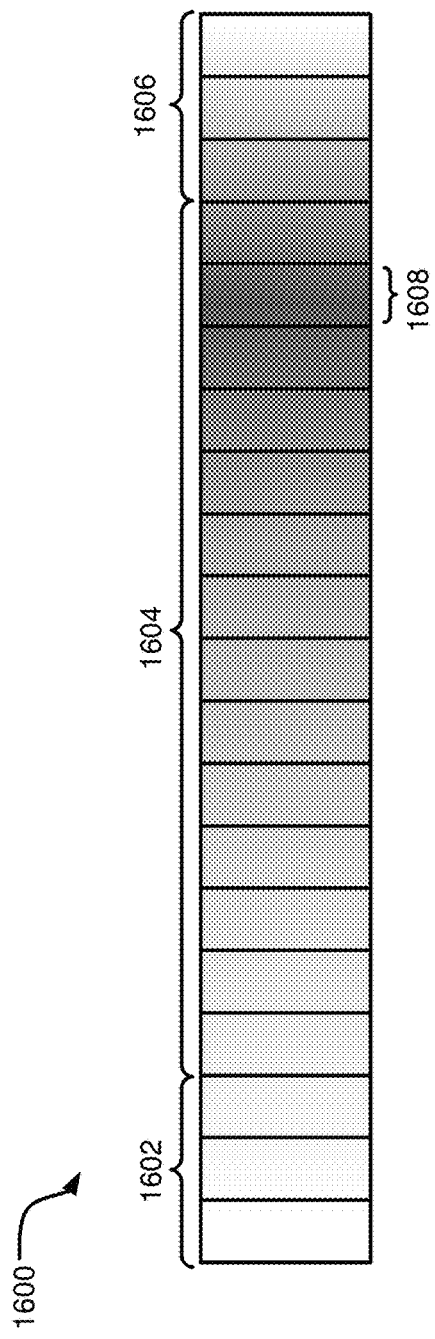
FIG. 16 illustrates a portion of the electromagnetic spectrum divided into a plurality of different sub-spectrums which may be emitted by emitters of a light source in accordance with the principles and teachings of the disclosure.

FIG. 16 illustrates a portion of the electromagnetic spectrum 1600 divided into twenty different sub-spectrums. The number of sub-spectrums is illustrative only. In at least one embodiment, the spectrum 1600 may be divided into hundreds of sub-spectrums, each with a small waveband. The spectrum may extend from the infrared spectrum 1602, through the visible spectrum 1604, and into the ultraviolet spectrum 1606. The sub-spectrums each have a waveband 1608 that covers a portion of the spectrum 1600. Each waveband may be defined by an upper wavelength and a lower wavelength.

Hyperspectral imaging includes imaging information from across the electromagnetic spectrum 1600. A hyperspectral pulse of electromagnetic radiation may include a plurality of sub-pulses spanning one or more portions of the electromagnetic spectrum 1600 or the entirety of the electromagnetic spectrum 1600. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 1600 and may include multiple exposure frames for multiple partitions of the electromagnetic spectrum 1600. In an embodiment, a hyperspectral exposure frame includes multiple hyperspectral exposure frames such that the combined hyperspectral exposure frame comprises data for the entirety of the electromagnetic spectrum 1600.

In one embodiment, at least one emitter (such as a laser emitter) is included in a light source (such as the light sources 202, 1700) for each sub-spectrum to provide complete and contiguous coverage of the whole spectrum 1600. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 17:
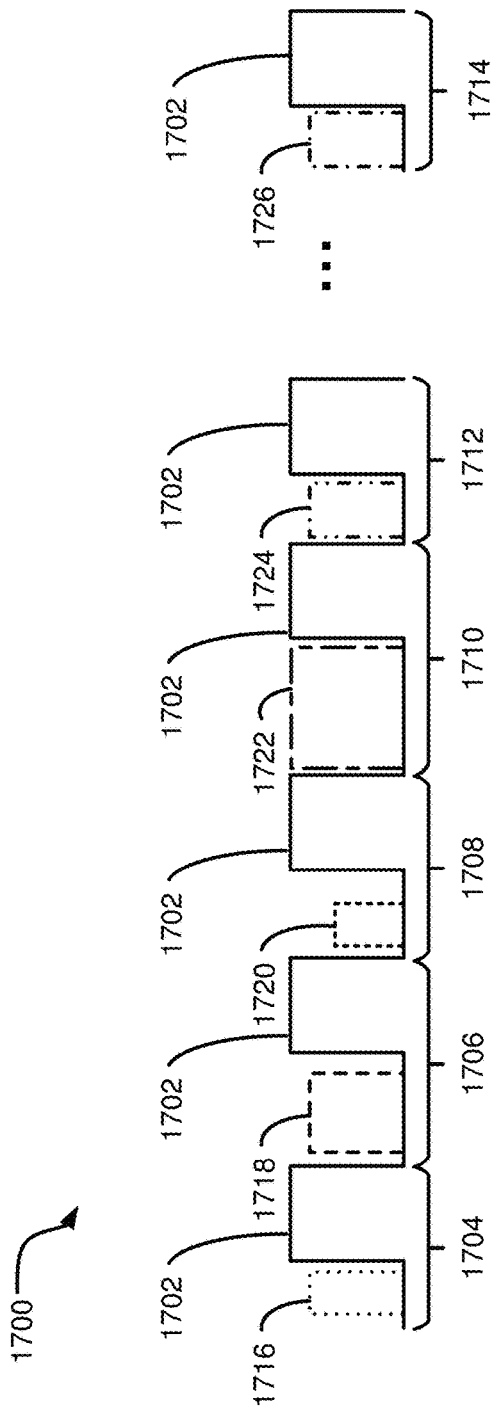
FIG. 17 is a schematic diagram illustrating a timing sequence for emission and readout for generating an image frame comprising a plurality of exposure frames resulting from differing partitions of pulsed light.

FIG. 17 is a schematic diagram illustrating a timing diagram 1700 for emission and readout for generating an image. The solid line represents readout (peaks 1702) and blanking periods (valleys) for capturing a series of exposure frames 1704-1714. The series of exposure frames 1704-1714 may include a repeating series of exposure frames which may be used for generating laser scanning, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser scanning data. The multiple exposure frames are combined to produce the single image frame. The single image frame is an RGB image with hyperspectral imaging data. The series of exposure frames include a first exposure frame 1704, a second exposure frame 1706, a third exposure frame 1708, a fourth exposure frame 1710, a fifth exposure frame 1712, and an Nth exposure frame 1726.

Additionally, the hyperspectral image data, the fluorescence image data, and the laser scanning data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser scanning data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser scanning data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (1702). Thus, each blanking period and readout results in an exposure frame for a specific spectrum of electromagnetic energy. For example, the first exposure frame 1704 may be generated based on a spectrum of a first one or more pulses 1716, a second exposure frame 1706 may be generated based on a spectrum of a second one or more pulses 1718, a third exposure frame 1708 may be generated based on a spectrum of a third one or more pulses 1720, a fourth exposure frame 1710 may be generated based on a spectrum of a fourth one or more pulses 1722, a fifth exposure frame 1712 may be generated based on a spectrum of a fifth one or more pulses 1724, and an Nth exposure frame 1726 may be generated based on a spectrum of an Nth one or more pulses 1726.

The pulses 1716-1726 may include energy from a single emitter or from a combination of two or more emitters. For example, the spectrum included in a single readout period or within the plurality of exposure frames 1704-1714 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 1716 may include red light, pulse 1718 may include blue light, and pulse 1720 may include green light while the remaining pulses 1722-1726 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 1704-1714 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser scanning pulsing scheme for generating a topology of the scene and calculating dimensions for objects within the scene. The location of the cancerous cells (as identified by the fluorescence imaging data) may be combined with the topology and dimensions information calculated based on the laser scanning data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser scanning pulsing scheme for generating a topology of the scene and calculating dimensions of objects within the scene. The location of the diseased tissue (as identified by the hyperspectral imaging data) may be combined with the topology and dimensions information that is calculated with the laser scanning data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 18A:
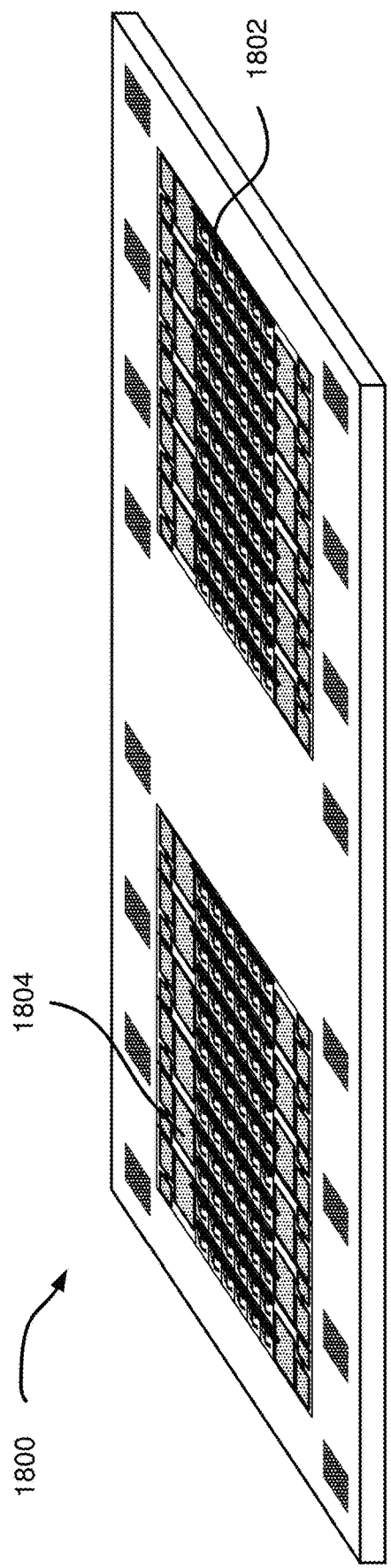
FIGS. 18A and 18B illustrate an implementation having a plurality of pixel arrays for producing a three-dimensional image in accordance with the principles and teachings of the disclosure.
Figure 18B:
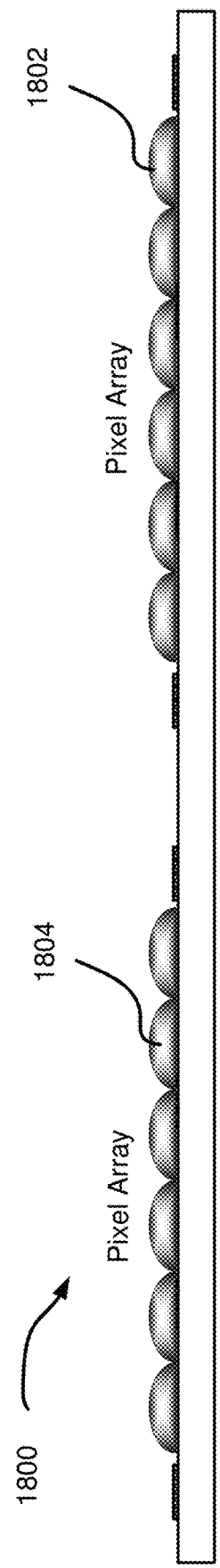

FIGS. 18A and 18B illustrate a perspective view and a side view, respectively, of an implementation of a monolithic sensor 1800 having a plurality of pixel arrays for producing a three-dimensional image in accordance with the teachings and principles of the disclosure. Such an implementation may be desirable for three-dimensional image capture, wherein the two-pixel arrays 1802 and 1804 may be offset during use. In another implementation, a first pixel array 1802 and a second pixel array 1804 may be dedicated to receiving a predetermined range of wave lengths of electromagnetic radiation, wherein the first pixel array is dedicated to a different range of wavelength electromagnetic radiation than the second pixel array.

Figure 19A:
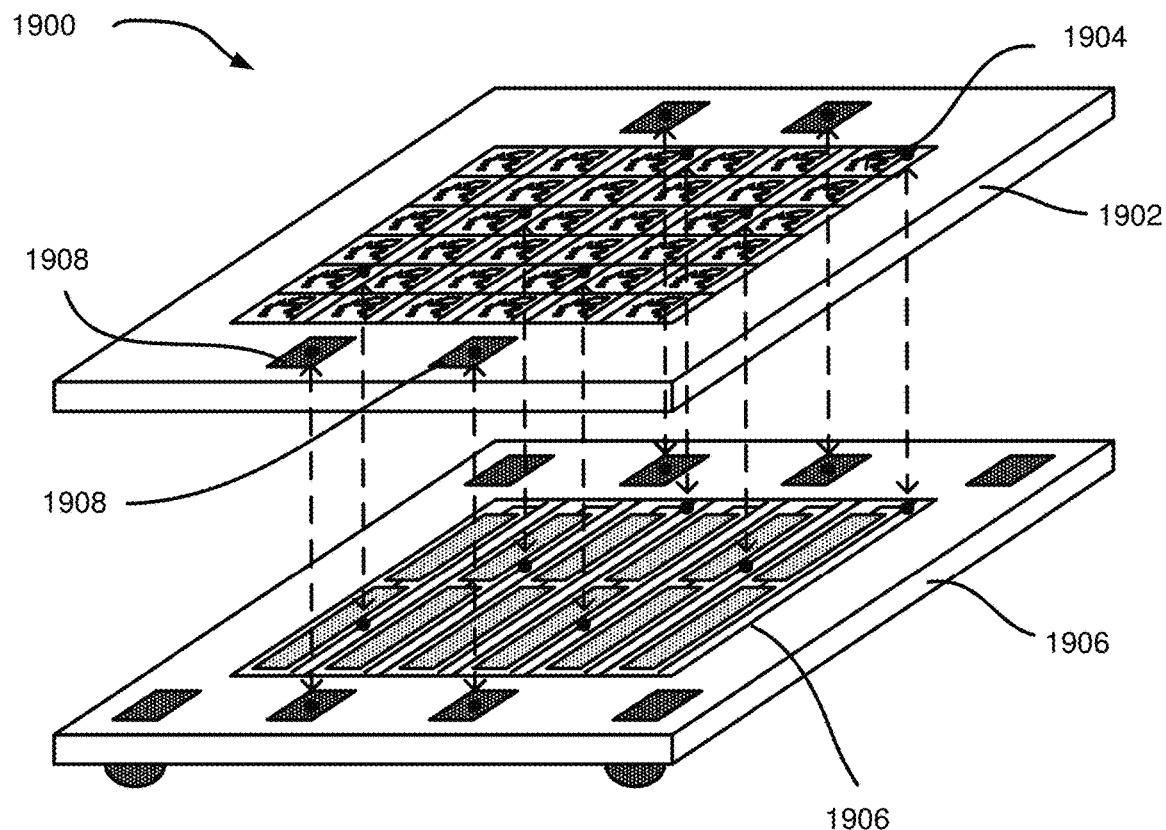
FIGS. 19A and 19B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 19B:
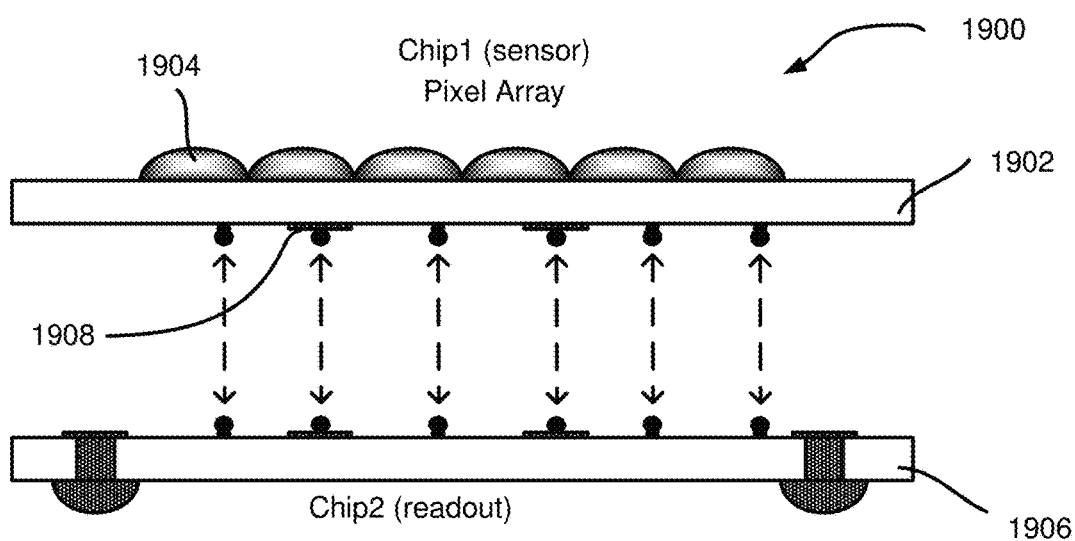

FIGS. 19A and 19B illustrate a perspective view and a side view, respectively, of an implementation of an imaging sensor 1900 built on a plurality of substrates. As illustrated, a plurality of pixel columns 1904 forming the pixel array are located on the first substrate 1902 and a plurality of circuit columns 1908 are located on a second substrate 1906. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 1902 of the two substrates/chips may be processed using an image CMOS process. The first substrate/chip 1902 may be comprised either of a pixel array exclusively or a pixel array surrounded by limited circuitry. The second or subsequent substrate/chip 1906 may be processed using any process and does not have to be from an image CMOS process. The second substrate/chip 1906 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 1902 may be stacked with the second or subsequent substrate/chip 1906 using any three-dimensional technique. The second substrate/chip 1906 may support most, or a majority, of the circuitry that would have otherwise been implemented in the first image CMOS chip 1902 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

FIGS. 20A and 20B illustrate a perspective view and a side view, respectively, of an implementation of an imaging sensor 2000 having a plurality of pixel arrays for producing a three-dimensional image. The three-dimensional image sensor may be built on a plurality of substrates and may comprise the plurality of pixel arrays and other associated circuitry, wherein a plurality of pixel columns 2004a forming the first pixel array and a plurality of pixel columns 2004b forming a second pixel array are located on respective substrates 2002a and 2002b, respectively, and a plurality of circuit columns 2008a and 2008b are located on a separate substrate 2006. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

EXAMPLES

The following examples pertain to preferred features of further embodiments:

Example 1 is a method. The method includes actuating an emitter to emit a plurality of pulses of electromagnetic radiation. The method includes sensing reflected electromagnetic radiation resulting from the plurality of pulses of electromagnetic radiation with a pixel array of an image sensor to generate a plurality of exposure frames. The method includes detecting motion across two or more sequential exposure frames of the plurality of exposure frames. The method includes compensating for the detected motion. The method includes combining the two or more sequential exposure frames to generate an image frame. The method is such that at least a portion of the plurality of pulses of electromagnetic radiation emitted by the emitter comprises one or more of: electromagnetic radiation having a wavelength from about 513 nm to about 545 nm; electromagnetic radiation having a wavelength from about 565 nm to about 585 nm; or electromagnetic radiation having a wavelength from about 900 nm to about 1000 nm.

Example 2 is a method as in Example 1, wherein compensating for the detected motion comprises: upscaling a first exposure frame of the two or more sequential exposure frames using interpolation to generate a first upscaled frame; upscaling the first exposure frame without using interpolation to generate a second upscaled frame, wherein the second upscaled frame comprises a first set of empty pixels; and filling in the first set of empty pixels of the second upscaled frame with pixel data from the first upscaled frame.

Example 3 is a method as in any of Examples 1-2, wherein compensating for the detected motion further comprises: upscaling a second exposure frame of the two or more sequential exposure frames to generate a third upscaled frame; and filling in a second set of empty pixels in the second upscaled frame with pixel data from the third upscaled frame.

Example 4 is a method as in any of Examples 1-3, wherein the two or more sequential exposure frames comprises a red exposure frame, a green exposure frame, and a blue exposure frame, and wherein combining the two or more sequential exposure frames to generate the image frame comprises generating a Red Green Blue ("RGB") image frame.

Example 5 is a method as in any of Examples 1-4, wherein the two or more sequential exposure frames comprises a luminance (Y) exposure frame, a chrominance blue (Cb) exposure frame, and a chrominance red (Cr) exposure frame, and wherein combining the two or more sequential exposure frames to generate the image frame comprises generating a YCbCr image frame.

Example 6 is a method as in any of Examples 1-5, wherein sensing the reflected electromagnetic radiation comprises: generating a first exposure frame based on a pulse of electromagnetic radiation of a first color partition; generating a second exposure frame based on a pulse of electromagnetic radiation of a second color partition; and generating a third exposure frame based on a pulse of electromagnetic radiation of the first color partition; wherein the second exposure frame is captured between the first exposure frame and the third exposure frame; wherein detecting motion across the two or more sequential exposure frames comprises calculating a relative motion estimate based on the first exposure frame and the third exposure frame using block matching; and wherein compensating for the detected motion comprises generating a motion compensated frame for the second exposure frame based on the relative motion estimate.

Example 7 is a method as in any of Examples 1-6, further comprising: determining a first motion vector for the first exposure frame and a second motion vector for the second exposure frame; and shifting a block of pixels in the first exposure frame by the first motion vector.

Example 8 is a method as in any of Examples 1-7, further comprising: performing bilinear interpolation on luminance data in the two or more sequential exposure frames to generate a first upscaled dataset; performing bicubic interpolation on the luminance data to generate a second upscaled dataset; and calculating a baseline with no interpolation of the luminance data to generate a third upscaled dataset.

Example 9 is a method as in any of Examples 1-8, wherein detecting motion across two or more sequential exposure frames comprises one or more of: segmenting data sensed by the pixel array into segments of pixels and nearest neighboring exposure frames; shifting each segment of pixels in the x direction and comparing with a neighboring exposure frame at a same resolution to identify motion of an object being imaged in the x direction; shifting each segment of pixels in the x direction in sub-pixel increments and comparing to the first upscaled dataset to identify motion of the object being imaged in the x direction with increased precision; shifting each segment of pixels in the y direction and comparing with a neighboring exposure frame to identify motion of an object being imaged in the y direction; or shifting each segment of pixels in the y direction in sub-pixel increments and comparing to the first upscaled dataset to identify motion of the object being imaged in the y direction with increased precision.

Example 10 is a method as in any of Examples 1-9, wherein sensing the reflected electromagnetic radiation comprises sensing during a readout period of the pixel array, wherein the readout period is a duration of time when active pixels in the pixel array are read.

Example 11 is a method as in any of Examples 1-10, wherein actuating the emitter comprises actuating the emitter to emit, during a pulse duration, a plurality of sub-pulses of electromagnetic radiation having a sub-duration shorter than the pulse duration.

Example 12 is a method as in any of Examples 1-11, wherein actuating the emitter comprises actuating the emitter to emit two or more wavelengths simultaneously as a single pulse or a single sub-pulse.

Example 13 is a method as in any of Examples 1-12, wherein sensing the reflected electromagnetic radiation comprises generating a hyperspectral exposure frame based on a hyperspectral pulse emitted by the emitter, and wherein the method further comprises providing the hyperspectral exposure frame to a corresponding system that determines a location of a critical tissue structure within a scene based on the hyperspectral exposure frame.

Example 14 is a method as in any of Examples 1-13, further comprising: receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 15 is a method as in any of Examples 1-14, wherein the critical tissue structure comprises one or more of a nerve, a ureter, a blood vessel, an artery, a blood flow, or a tumor.

Example 16 is a method as in any of Examples 1-15, further comprising synchronizing timing of the plurality of pulses of electromagnetic radiation to be emitted during a blanking period of the image sensor, wherein the blanking period corresponds to a time between a readout of a last row of active pixels in the pixel array and a beginning of a next subsequent readout of active pixels in the pixel array.

Example 17 is a method as in any of Examples 1-16, wherein the two or more sequential exposure frames are captured sequentially in time based on two or more pulses of electromagnetic radiation emitted by the emitter sequentially in time.

Example 18 is a method as in any of Examples 1-17, wherein sensing the reflected electromagnetic radiation comprises sensing with a first pixel array and a second pixel array such that a three-dimensional image can be generated based on the sensed reflected electromagnetic radiation.

Example 19 is a method as in any of Examples 1-18, wherein actuating the emitter comprises actuating the emitter to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 20 is a method as in any of Examples 1-19, wherein actuating the emitter comprises actuating the emitter to emit a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image comprising an overlay of hyperspectral imaging data, wherein the hyperspectral wavelength of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm; or Example 21 is a system. The system includes an emitter for emitting a plurality of pulses of electromagnetic radiation. The system includes an image sensor comprising a pixel array for sensing reflected electromagnetic radiation to generate a plurality of exposure frames. The system includes one or more processors configurable to execute instructions stored in non-transitory computer readable storage media, the instructions comprising: detecting motion across two or more sequential exposure frames of the plurality of exposure frames; compensating for the detection motion; and combining the two or more sequential exposure frames to generate an image frame; wherein at least a portion of the pulses of electromagnetic radiation emitted by the emitter comprises one or more of: electromagnetic radiation having a wavelength from about 513 nm to about 545 nm; electromagnetic radiation having a wavelength from about 565 nm to about 585 nm; or electromagnetic radiation having a wavelength from about 900 nm to about 1000 nm.

Example 22 is a system as in Example 21, wherein the instructions are such that compensating for the detected motion comprises: upscaling a first exposure frame of the two or more sequential exposure frames using interpolation to generate a first upscaled frame; upscaling the first exposure frame without using interpolation to generate a second upscaled frame, wherein the second upscaled frame comprises a first set of empty pixels; filling in the first set of empty pixels of the second upscaled frame with pixel data from the first upscaled frame; upscaling a second exposure frame of the two or more sequential exposure frames to generate a third upscaled frame; and filling in a second set of empty pixels in the second upscaled frame with pixel data from the third upscaled frame.

Example 23 is a system as in any of Examples 21-22, wherein one or more of: the two or more sequential exposure frames comprises a luminance (Y) exposure frame, a chrominance blue (Cb) exposure frame, and a chrominance red (Cr) exposure frame, and wherein combining the two or more sequential exposure frames to generate the image frame comprises generating a YCbCr image frame; or the two or more sequential exposure frames comprises a red exposure frame, a green exposure frame, and a blue exposure frame, and wherein combining the two or more sequential exposure frames to generate the image frame comprises generating a Red Green Blue ("RGB") image frame.

Example 24 is a system as in any of Examples 21-23, wherein the image sensor is configured to: generate a first exposure frame based on a pulse of electromagnetic radiation of a first color partition; generate a second exposure frame based on a pulse of electromagnetic radiation of a second color partition; and generate a third exposure frame based on a pulse of electromagnetic radiation of the first color partition; wherein the second exposure frame is captured between the first exposure frame and the third exposure frame; wherein the instructions are such that detecting motion across the two or more sequential exposure frames comprises calculating a relative motion estimate based on the first exposure frame and the third exposure frame using block matching; and wherein the instructions are such that compensating for the detected motion comprises generating a motion compensated frame for the second exposure frame based on the relative motion estimate.

Example 25 is a system as in any of Examples 21-24, wherein at least a portion of the pulses of electromagnetic radiation emitted by the emitter results in a hyperspectral exposure frame created by the image sensor, and wherein the instructions further comprise providing the hyperspectral exposure frame to a corresponding system that determines a location of a critical tissue structure within a scene based on the hyperspectral exposure frame.

Example 26 is a system as in any of Examples 21-25, wherein the instructions further comprise: receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 27 is a system as in any of Examples 21-26, wherein the critical tissue structure comprises one or more of a nerve, a ureter, a blood vessel, an artery, a blood flow, or a tumor.

Example 28 is a system as in any of Examples 21-27, wherein the image sensor comprises a first image sensor and a second image sensor such that the image sensor can generate a three-dimensional image.

Example 29 is a system as in any of Examples 21-28, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 30 is a system as in any of Examples 21-29, wherein at least a portion of the plurality of pulses of electromagnetic radiation comprise a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image comprising an overlay of hyperspectral imaging data, wherein the hyperspectral wavelength of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. An endoscopic method for providing visualization to a light deficient environment comprising:
    actuating an emitter to emit a plurality of pulses of electromagnetic radiation;
    wherein the emitter comprises a visible source of electromagnetic radiation and one or more multispectral sources of electromagnetic radiation for eliciting a spectral response from one or more tissues;
    sensing reflected electromagnetic radiation resulting from the plurality of pulses of electromagnetic radiation with a pixel array of an image sensor to generate a plurality of exposure frames;
    detecting motion across two or more sequential exposure frames of the plurality of exposure frames;
    compensating for the detected motion; and
    combining the two or more sequential exposure frames to generate an image frame;
    wherein at least a portion of the plurality of pulses of electromagnetic radiation emitted by the emitter comprises electromagnetic radiation having a wavelength from 900 nm to 1000 nm and one or more of:
    electromagnetic radiation having a wavelength from 513 nm to 545 nm; or
    electromagnetic radiation having a wavelength from 565 nm to 585 nm.

2. The method of claim 1, wherein compensating for the detected motion comprises:
    upscaling a first exposure frame of the two or more sequential exposure frames using interpolation to generate a first upscaled frame;
    upscaling the first exposure frame without using interpolation to generate a second upscaled frame, wherein the second upscaled frame comprises a first set of empty pixels; and
    filling in the first set of empty pixels of the second upscaled frame with pixel data from the first upscaled frame.

3. The method of claim 2, wherein compensating for the detected motion further comprises:
    upscaling a second exposure frame of the two or more sequential exposure frames to generate a third upscaled frame; and
    filling in a second set of empty pixels in the second upscaled frame with pixel data from the third upscaled frame.

4. The method of claim 1, wherein:
    the two or more sequential exposure frames comprise a red exposure frame, a green exposure frame, and a blue exposure frame; and wherein combining the two or more sequential exposure frames to generate the image frame comprises generating a Red Green Blue ("RGB") image frame.

5. The method of claim 1, wherein:
the two or more sequential exposure frames comprise a luminance (Y) exposure frame, a chrominance blue (Cb) exposure frame, and a chrominance red (Cr) exposure frame; and
wherein combining the two or more sequential exposure frames to generate the image frame comprises generating a YCbCr image frame.

6. The method of claim 1, wherein sensing the reflected electromagnetic radiation comprises:
generating a first exposure frame based on a pulse of electromagnetic radiation of a first color partition;
generating a second exposure frame based on a pulse of electromagnetic radiation of a second color partition; and
generating a third exposure frame based on a pulse of electromagnetic radiation of the first color partition;
wherein the second exposure frame is captured between the first exposure frame and the third exposure frame;
wherein detecting motion across the two or more sequential exposure frames comprises calculating a relative motion estimate based on the first exposure frame and the third exposure frame using block matching; and
wherein compensating for the detected motion comprises generating a motion compensated frame for the second exposure frame based on the relative motion estimate.

7. The method of claim 6, further comprising:
determining a first motion vector for the first exposure frame and a second motion vector for the second exposure frame; and
shifting a block of pixels in the first exposure frame by the first motion vector.

8. The method of claim 1, further comprising:
performing bilinear interpolation on luminance data in the two or more sequential exposure frames to generate a first upscaled dataset;
performing bicubic interpolation on the luminance data to generate a second upscaled dataset; and
calculating a baseline with no interpolation of the luminance data to generate a third upscaled dataset.

9. The method of claim 8, wherein detecting motion across two or more sequential exposure frames comprises one or more of:
segmenting data sensed by the pixel array into segments of pixels and nearest neighboring exposure frames;
shifting each segment of pixels in the x direction and comparing with a neighboring exposure frame at a same resolution to identify motion of an object being imaged in the x direction;
shifting each segment of pixels in the x direction in sub-pixel increments and comparing to the first upscaled dataset to identify motion of the object being imaged in the x direction with increased precision;
shifting each segment of pixels in the y direction and comparing with a neighboring exposure frame to identify motion of an object being imaged in the y direction; or
shifting each segment of pixels in the y direction in sub-pixel increments and comparing to the first upscaled dataset to identify motion of the object being imaged in the y direction with increased precision.

10. The method of claim 1, wherein sensing the reflected electromagnetic radiation comprises sensing during a readout period of the pixel array, wherein the readout period is a duration of time when active pixels in the pixel array are read.

11. The method of claim 1, wherein actuating the emitter comprises actuating the emitter to emit, during a pulse duration, a plurality of sub-pulses of electromagnetic radiation having a sub-duration shorter than the pulse duration.

12. The method of claim 1, wherein actuating the emitter comprises actuating the emitter to emit two or more wavelengths simultaneously as a single pulse or a single sub-pulse.

13. The method of claim 1, wherein:
sensing the reflected electromagnetic radiation comprises generating a hyperspectral exposure frame based on a hyperspectral pulse emitted by the emitter; and
wherein the method further comprises providing the hyperspectral exposure frame to a corresponding system that determines a location of a tissue structure within a scene based on the hyperspectral exposure frame.

14. The method of claim 13, further comprising:
receiving the location of the tissue structure from the corresponding system;
generating an overlay frame comprising the location of the tissue structure; and
combining the overlay frame with a color image frame depicting the scene to indicate the location of the tissue structure within the scene.

15. The method of claim 14, wherein the tissue structure comprises one or more of a nerve, a ureter, a blood vessel, an artery, a blood flow, or a tumor.

16. The method of claim 1, further comprising synchronizing timing of the plurality of pulses of electromagnetic radiation to be emitted during a blanking period of the image sensor, wherein the blanking period corresponds to a time between a readout of a last row of active pixels in the pixel array and a beginning of a next subsequent readout of active pixels in the pixel array.

17. The method of claim 1, wherein the two or more sequential exposure frames are captured sequentially in time based on two or more pulses of electromagnetic radiation emitted by the emitter sequentially in time.

18. The method of claim 1, wherein sensing the reflected electromagnetic radiation comprises sensing with a first pixel array and a second pixel array such that a three-dimensional image can be generated based on the sensed reflected electromagnetic radiation.

19. The method of claim 1, wherein:
actuating the emitter comprises actuating the emitter to emit a sequence of pulses of electromagnetic radiation repeatedly sufficient for generating a video stream comprising a plurality of image frames, wherein each image frame in the video stream comprises data from a plurality of exposure frames; and
wherein each of the exposure frames corresponds to a pulse of electromagnetic radiation.

20. The method of claim 1, wherein actuating the emitter comprises actuating the emitter to emit a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image comprising an overlay of hyperspectral imaging data, wherein the hyperspectral wavelength of electromagnetic radiation comprises:

the electromagnetic radiation having the wavelength from 513 nm to 545 nm and the electromagnetic radiation having the wavelength from 900 nm to 1000 nm; or the electromagnetic radiation having the wavelength from 565 nm to 585 nm and the electromagnetic radiation having the wavelength from 900 nm to 1000 nm.

21. An endoscopic system comprising:

an emitter for emitting a plurality of pulses of electromagnetic radiation;

wherein the emitter comprises a visible source of electromagnetic radiation and one or more multispectral sources of electromagnetic radiation for eliciting a spectral response from one or more tissues;

an image sensor comprising a pixel array for sensing reflected electromagnetic radiation to generate a plurality of exposure frames; and one or more processors configurable to execute instructions stored in non-transitory computer readable storage media, the instructions comprising:

detecting motion across two or more sequential exposure frames of the plurality of exposure frames;

compensating for the detection motion; and combining the two or more sequential exposure frames to generate an image frame;

wherein at least a portion of the pulses of electromagnetic radiation emitted by the emitter comprises electromagnetic radiation having a wavelength from 900 nm to 1000 nm and one or more of:

electromagnetic radiation having a wavelength from 513 nm to 545 nm; or electromagnetic radiation having a wavelength from 565 nm to 585 nm.

22. The system of claim 21, wherein the instructions are such that compensating for the detected motion comprises:

upscaling a first exposure frame of the two or more sequential exposure frames using interpolation to generate a first upscaled frame;

upscaling the first exposure frame without using interpolation to generate a second upscaled frame, wherein the second upscaled frame comprises a first set of empty pixels;

filling in the first set of empty pixels of the second upscaled frame with pixel data from the first upscaled frame;

upscaling a second exposure frame of the two or more sequential exposure frames to generate a third upscaled frame; and filling in a second set of empty pixels in the second upscaled frame with pixel data from the third upscaled frame.

23. The system of claim 21, wherein one or more of:

the two or more sequential exposure frames comprise:

a luminance (Y) exposure frame, a chrominance blue (Cb) exposure frame, and a chrominance red (Cr) exposure frame, and wherein combining the two or more sequential exposure frames to generate the image frame comprises generating a YCbCr image frame; or the two or more sequential exposure frames comprise:

a red exposure frame, a green exposure frame, and a blue exposure frame, and wherein combining the two or more sequential exposure frames to generate the image frame comprises generating a Red Green Blue ("RGB") image frame.

24. The system of claim 21, wherein the image sensor is configured to:

generate a first exposure frame based on a pulse of electromagnetic radiation of a first color partition;

generate a second exposure frame based on a pulse of electromagnetic radiation of a second color partition; and generate a third exposure frame based on a pulse of electromagnetic radiation of the first color partition;

wherein the second exposure frame is captured between the first exposure frame and the third exposure frame;

wherein the instructions are such that detecting motion across the two or more sequential exposure frames comprises calculating a relative motion estimate based on the first exposure frame and the third exposure frame using block matching; and wherein the instructions are such that compensating for the detected motion comprises generating a motion compensated frame for the second exposure frame based on the relative motion estimate.

25. The system of claim 21, wherein:

at least a portion of the pulses of electromagnetic radiation emitted by the emitter results in a hyperspectral exposure frame created by the image sensor; and wherein the instructions further comprise providing the hyperspectral exposure frame to a corresponding system that determines a location of a critical tissue structure within a scene based on the hyperspectral exposure frame.

26. The system of claim 25, wherein the instructions further comprise:

receiving the location of the tissue structure from the corresponding system;

generating an overlay frame comprising the location of the tissue structure; and combining the overlay frame with a color image frame depicting the scene to indicate the location of the tissue structure within the scene.

27. The system of claim 26, wherein the tissue structure comprises one or more of a nerve, a ureter, a blood vessel, an artery, a blood flow, or a tumor.

28. The system of claim 21, wherein the image sensor comprises a first image sensor and a second image sensor such that the image sensor can generate a three-dimensional image.

29. The system of claim 21, wherein:

the emitter is configured to emit a sequence of pulses of electromagnetic radiation repeatedly sufficient for generating a video stream comprising a plurality of image frames, wherein each image frame in the video stream comprises data from a plurality of exposure frames; and wherein each of the exposure frames corresponds to a pulse of electromagnetic radiation.

30. The system of claim 21, wherein at least a portion of the plurality of pulses of electromagnetic radiation comprises a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image comprising an overlay of hyperspectral imaging data, wherein the hyperspectral wavelength of electromagnetic radiation comprises:

the electromagnetic radiation having the wavelength from 513 nm to 545 nm and the electromagnetic radiation having the wavelength from 900 nm to 1000 nm; or the electromagnetic radiation having the wavelength from 565 nm to 585 nm and the electromagnetic radiation having the wavelength from 900 nm to 1000 nm.

\* \* \* \* \*